United States Patent
Khait et al.

(10) Patent No.: US 12,191,566 B2
(45) Date of Patent: Jan. 7, 2025

(54) COMPACT HELIX ANTENNA FOR IN-VIVO DEVICES

(71) Applicant: Given Imaging LTD., Yoqneam (IL)

(72) Inventors: Semion Khait, Natanya (IL); Iddo Diukman, Zihron Yaakov (IL)

(73) Assignee: Given Imaging Ltd., Yoqneam (IL)

( * ) Notice: Subject to any disclaimer, the term of this patent is extended or adjusted under 35 U.S.C. 154(b) by 206 days.

(21) Appl. No.: 17/876,691

(22) Filed: Jul. 29, 2022

(65) Prior Publication Data

US 2022/0368019 A1  Nov. 17, 2022

Related U.S. Application Data

(62) Division of application No. 16/332,571, filed as application No. PCT/IL2017/050938 on Aug. 22, 2017, now Pat. No. 11,437,726.

(Continued)

(51) Int. Cl.
*H01Q 11/08* (2006.01)
*A61B 1/00* (2006.01)
(Continued)

(52) U.S. Cl.
CPC .............. *H01Q 11/08* (2013.01); *H01Q 1/273* (2013.01); *A61B 1/00016* (2013.01);
(Continued)

(58) Field of Classification Search
CPC .......... H01Q 1/273; H01Q 7/00; H01Q 11/08; A61N 1/37229; A61N 1/3787
See application file for complete search history.

(56) References Cited

U.S. PATENT DOCUMENTS

| 5,754,146 A | 5/1998 | Knowles et al. |
| 6,566,933 B1 | 5/2003 | Lye |
| (Continued) | | |

FOREIGN PATENT DOCUMENTS

| CN | 106537532 A | 3/2017 |
| EP | 0674354 A2 | 9/1995 |
| WO | 2016006508 A1 | 1/2016 |

OTHER PUBLICATIONS

European Examination issued in corresponding Applicaiton No. EP 17850404.9 dated May 7, 2021 (5 pages).
(Continued)

*Primary Examiner* — Graham P Smith
*Assistant Examiner* — Amal Patel
(74) *Attorney, Agent, or Firm* — Carter, DeLuca & Farrell LLP

(57) ABSTRACT

A helix antenna structure includes loop antennas and a multilayered printed circuit board including printed circuit board layers. Each printed circuit board layer includes a peripheral loop antenna and each adjacent two loop antennas are electrically connected by a connection bridge functioning as a monopole antenna. A selected printed circuit board layer physically and electrically accommodates a transmitter inside 'its' peripheral loop antenna, and it further includes a first antenna feeding line which is connected to the loop antenna that is disposed on the selected printed circuit board layer and electrically connectable to a first output terminal of the transmitter. A second antenna feeding line is disposed on another printed circuit board layer and electrically connected to its loop antenna and connectable to another output terminal of the transmitter. The two antenna feeding lines lie in a plane perpendicular to an axis of the printed circuit board after its folding.

14 Claims, 20 Drawing Sheets

Related U.S. Application Data

(60) Provisional application No. 62/521,739, filed on Jun. 19, 2017, provisional application No. 62/393,877, filed on Sep. 13, 2016.

(51) Int. Cl.
  *A61B 1/04* (2006.01)
  *A61B 5/00* (2006.01)
  *A61N 1/372* (2006.01)
  *A61N 1/378* (2006.01)
  *H01Q 1/27* (2006.01)

(52) U.S. Cl.
  CPC ............. *A61B 1/041* (2013.01); *A61B 5/0031* (2013.01); *A61N 1/37229* (2013.01); *A61N 1/3787* (2013.01)

(56) References Cited

U.S. PATENT DOCUMENTS

| | | |
|---|---|---|
| 7,801,586 B2 | 9/2010 | Muratayev et al. |
| 2006/0028378 A1 | 2/2006 | Gaucher et al. |
| 2006/0082517 A1 | 4/2006 | Chung et al. |
| 2006/0241422 A1* | 10/2006 | Muratayev ............... H01Q 9/27 |
| | | 600/435 |
| 2009/0228074 A1 | 9/2009 | Edgell et al. |
| 2009/0281401 A1* | 11/2009 | Takenaka ............... A61B 1/041 |
| | | 600/302 |
| 2010/0019987 A1 | 1/2010 | Yamada et al. |
| 2015/0182145 A1 | 7/2015 | Gazdzinski |
| 2015/0381401 A1 | 12/2015 | Butterfield et al. |
| 2017/0133152 A1* | 5/2017 | Kouchi ............... H01F 27/2804 |

OTHER PUBLICATIONS

Office Action issued in corresponding Chinese Appl. No. 201780062686.9 dated Apr. 26, 2021, together with English language translation retrieved from the Global Dossier (11 pages).

Office Action issued in corresponding Japanese Application, JP 2019-513941 mailed Jul. 27, 2021, together with English language translation (6 pages).

International Search Report and Written Opinion for PCT International Application No. PCT/IL2017/050938 mailed Feb. 1, 2018.

Examination Report in European Application No. EP 17 850 404.9, dated Jul. 22, 2024, 5 pages.

\* cited by examiner

Helical antenna:
(B) Central support,
(C) Coaxial cable feedline,
(E) Insulating supports for the helix,
(R) Reflector ground plane,
(S) Helical radiating wire

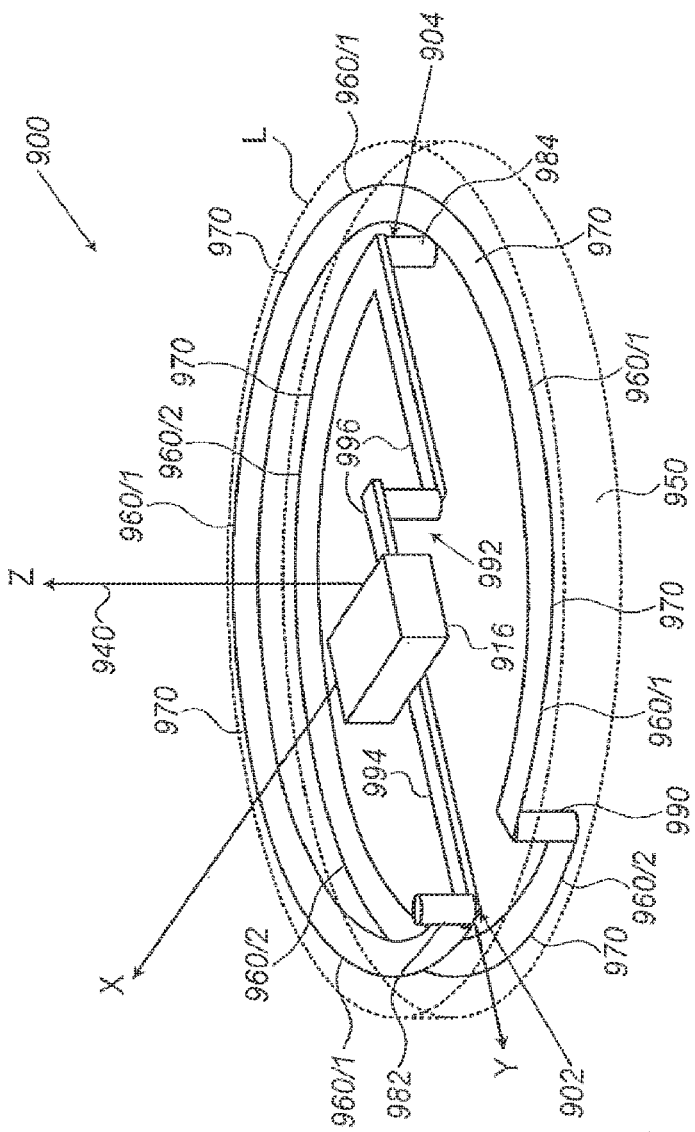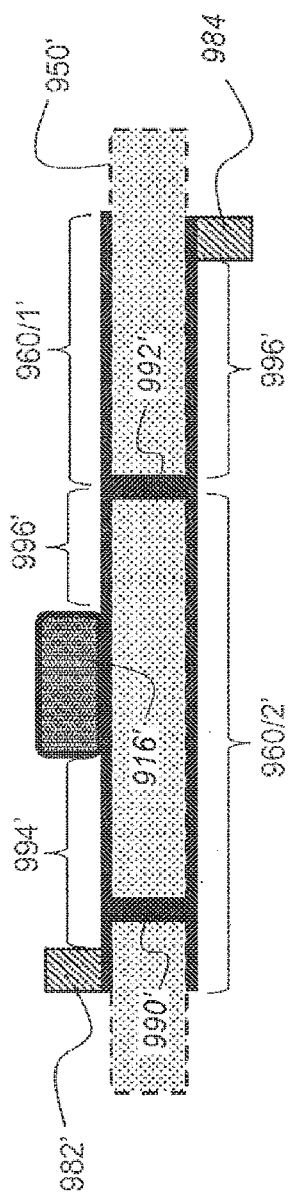
Fig. 9A
Fig 9B

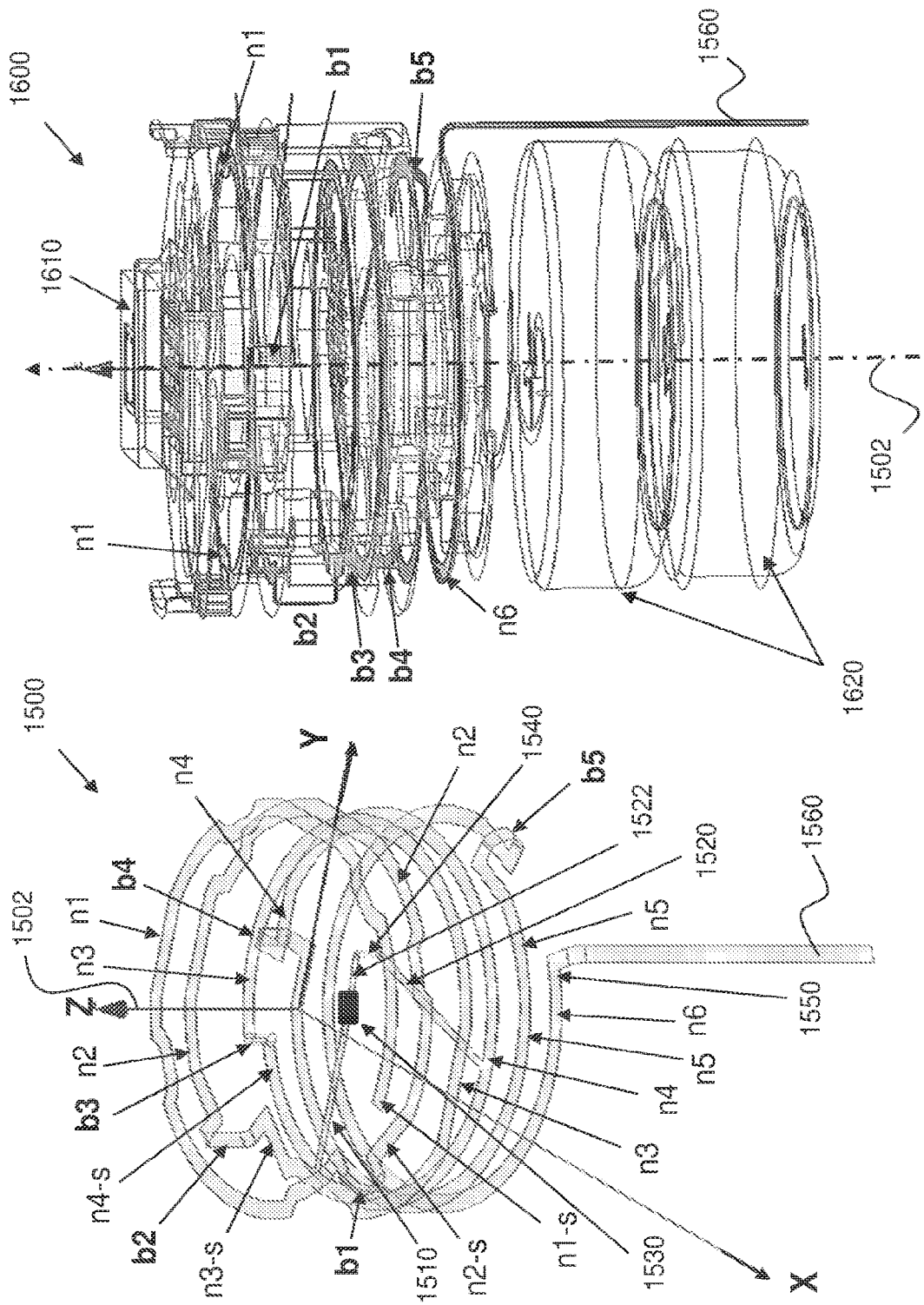

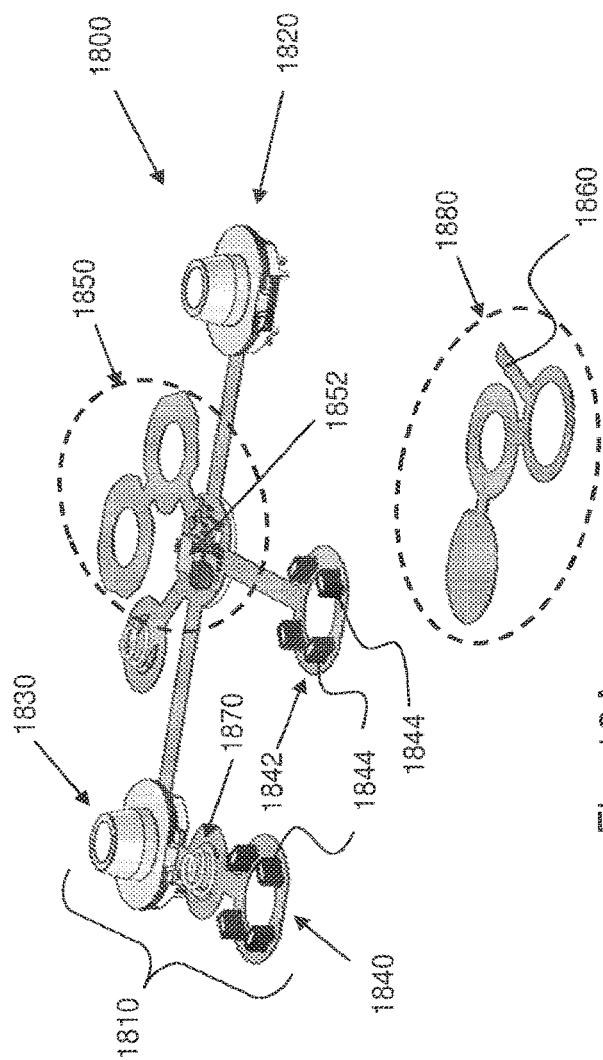
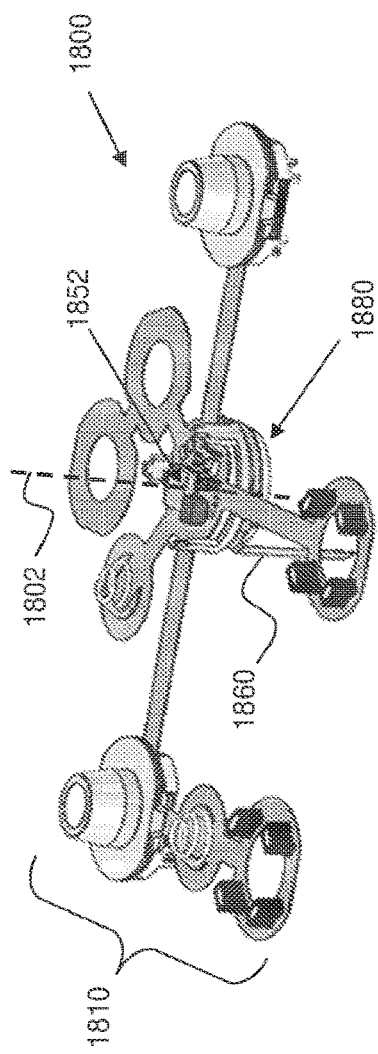
Fig. 18A
Fig. 18B

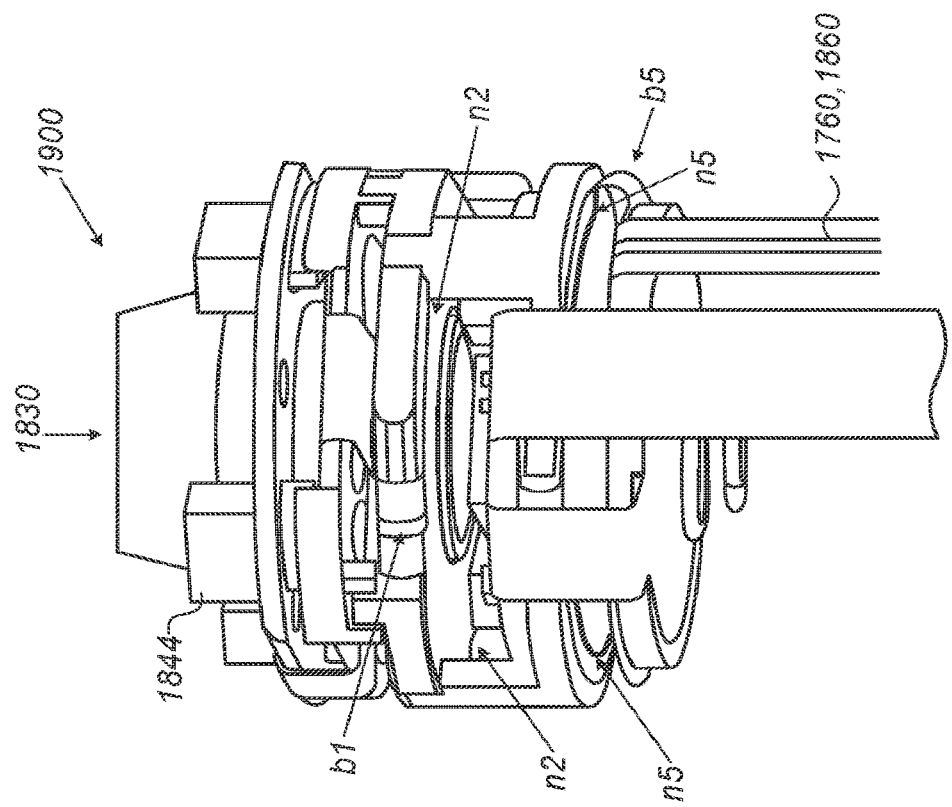
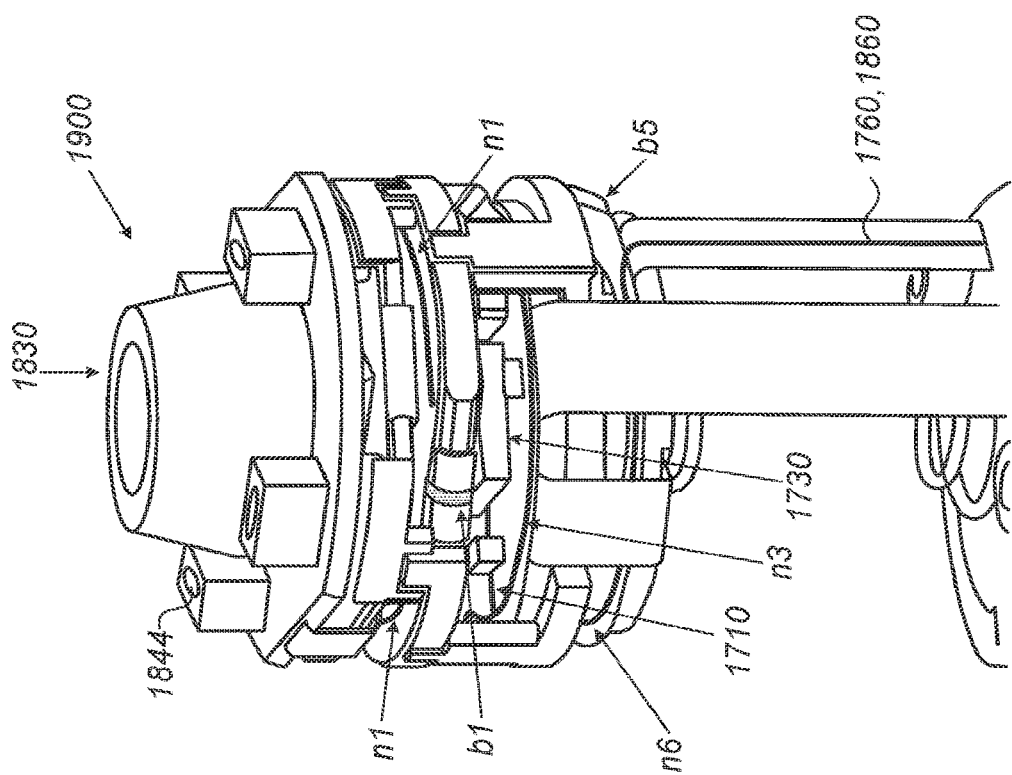
Fig. 19B
Fig. 19A

COMPACT HELIX ANTENNA FOR IN-VIVO DEVICES

CROSS-REFERENCE TO RELATED APPLICATIONS

This application is a Divisional of, and claims priority to, U.S. patent application Ser. No. 16/332,571, filed Mar. 12, 2019, which is a U.S. National Stage Application of International Patent Application No. PCT/IL2017/050938, filed Aug. 22, 2017, which in turn claims priority to U.S. Provisional Patent Application Nos. 62/393,877, filed Sep. 13, 2016, and 62/521,739, filed Jun. 19, 2017. The entire contents of each of the foregoing applications are hereby incorporated by reference herein.

FIELD OF THE INVENTION

The present invention generally relates to antennas, and more specifically to a compact helix antenna structure suitable for embedding, for example, in implantable devices and in swallowable in-vivo devices, and in small controllable devices (e.g., miniature controllable tools, miniature toys, and the like).

BACKGROUND

In-vivo imaging systems are known in the medical field as 'capsule endoscopy' systems. For example, capsule like in-vivo devices, which traverse the GI tract, may include, for example, an image sensor, or imager, for imaging (e.g., capturing images or taking pictures of) the interior of the GI tract, sensors of other types, light emitting diodes ("LEDs") for illuminating the interior of, for example, the gastrointestinal ("GI") tract, a battery and a transmitter to transmit data frames (e.g., image frame) to an external receiver (e.g., a wearable data recorder).

Conventional swallowable capsules use a linearly polarized antenna to transmit data frames, for example, to an external or remote receiver. Linear antennas are antennas that transmit signals by using linear polarization. Using a linearly polarized antenna in a swallowable capsule has a drawback that is related to the circumstances under which the capsule operates. For example, the GI tract often changes directions and, therefore, has many turns that the capsule must follow, which means that the movement direction of the capsule, and hence the capsule's spatial (3D) orientation, constantly changes as the capsule traverses the GI tract. The result of the frequent changes in the capsule orientation is degradation in the performance of the communication channel between the capsule (or another in-vivo device) and the external or remote receiver (which could cause occasional communication degradation due to occasional misalignment between the capsule's antenna and the receiver's antenna), meaning that the external receiver occasionally fails to receive data frames from the capsule. In addition, the small size of the swallowable capsule does not leave much space for a larger antenna, and the capsule's battery may have to be able to power the entire capsule for many hours (e.g., to support, e.g., a 7-10 hour medical procedure). Therefore, increasing the capsule's transmission power in order to reduce communication gaps may result in shortened capsule's operation time. (Assuming that the power consumption of the other components of the capsule remain the same).

Conventional capsules transmit data frames by using a modulation technique known as the minimal shift keying "(MSK"). While MSK communication supports a certain data bits transmission rate, there is a need to increase data transmission rate of the data that the capsule transmits without compromising communication performance (Increasing data transmission rate enables increasing (or using increased), for example, image capturing rate, or emptying a data memory buffer more quickly compared to lower data transmission rates.) Data transmission rate and immunity to electromagnetic interferences can be improved, for example, by using a much more advanced communication scheme such as an Orthogonal Frequency Division Multiplexing ("OFDM") communication scheme. However, transmitting OFDM signals requires an RF power amplifier ("PA"). Using a PA to transmit OFDM signals may, additionally, be beneficial, for example, in terms of transmission power management and controllability. However, the antenna currently used by capsules cannot interoperate with a PA due to impedance mismatch issues. (The capsule's transmitter has conventionally been implemented as a simple type of LC oscillator (e.g., Colpitts oscillator), which is an inferior 'type' of transmitter because it is more an oscillator than a transmitter.) Therefore, incorporation of a PA in a swallowable capsule (in order to facilitate OFDM communication) calls for a new antenna design, which would not take up much space in the capsule while, at the same time, would be able to interoperate with a PA and support OFDM communication.

U.S. Pat. No. 7,801,586 ('586) discloses a capsule (in-vivo device) with a conventional transmitting antenna. For example, as shown in FIG. 1 (prior art), a capsule having a housing 205 includes a vertical antenna 226, shown mounted on supporting board 204, includes a vertically oriented air coil. Antenna 226 circles along (and perpendicularly to) axis "A" of housing 205 of device, and extends vertically along axis B. According to U.S. patent '586, the in-vivo device may alternatively include an antenna 327, as shown in FIG. 2 (prior art). Antennas 226 and 327 have a drawback, which is that they enable optimal communication only when the capsule has certain orientation (with respect to a receiving antenna), while communication significantly degrades at many other orientations of the capsule. To solve that problem, '586 discloses an antenna 993, as shown in FIG. 3A (prior art). Unlike antennas 226 and 327, antenna 993 is not a coiled antenna but, rather, it has a different shape. Antenna 993 provides a "diversity polarization field" (polarization field 998, FIG. 3B) of a 3D antenna. ('586 reads—"By folding an antenna such as antenna 993, for example within device 40, an antenna which includes conductors in three dimensions is formed wherein each conductor radiates in a different direction. As a result of this, a uniform field such as a diversity polarization field 998 is generated around the antenna and/or around device 40.")

FIG. 4A shows a conventional helix antenna 410, and FIG. 4B depicts an example device (a cell phone 420) that uses a helix antenna (430). While a helix antenna can beneficially operate in circular mode, U.S. Patent Publication No. 2010/0019987 ('987) shows an ultra-small normal mode helical antenna with tap feeding (see FIG. 5 of the present application, corresponding to FIG. 7A of '987), and describes some drawbacks that hinder integration of such an antenna in a small device such as an implantable device or swallowable in-vivo device (e.g., swallowable capsule): "A structure in which tap feeding is made in the helical structure 200 in FIG. 1 is shown in FIG. 7B. Here, L1=20 mm and L2=20 mm are applied. The input impedance has been slightly increased by the tap feeding. However, since the value without tap feeding is as small as 2.146 ohm, the input impedance after increasing by the tap feeding remains around 50 ohm. If L1 and L2 are increased, an input impedance will be increased accordingly. However, in that case, a size of the tap portion may be too large relative to the antenna length of 50 mm. In addition, it is very difficult to increase the input impedance up to the 50 ohm feeder impedance. Consequently, according to the existing tap feeding structure, it is very difficult to increase an input impedance of an ultra-small normal mode helical antenna smaller than or equal to 0.05 wavelength ($\lambda$), and thus impedance matching a feeder cannot be effectively carried out for those antennas. As described above, in a normal mode helical antenna of about 0.2 wavelength in length, it is relatively easy to have the input impedance matched with the 50 ohm feeder impedance since the tap portion length is allowed to be substantially long. However, in a normal mode helical antenna, in which the length is less than or equal to 0.05 wavelength, it is difficult to give a sufficient length to a tap portion and therefore a resistance value thereof cannot be sufficiently increased, thus matching the 50 ohm feeder cannot be accomplished. As explained above, in a normal mode helical antenna, it is sometimes difficult to realize a required input impedance due to restriction on antenna size."

While certain properties of a helix antenna are beneficial for an in-vivo device or implantable device, there are some drawbacks associated with such antennas, for example as specified above, that need to be overcome in order for it to be incorporated in implantable devices or in swallowable devices. It would, therefore, be beneficial to have a simple, yet efficient (e.g., in terms of power consumption, size, impedance matching), antenna construction that overcomes the drawbacks described above.

SUMMARY

There is disclosed a helix antenna structure which incorporates a helix antenna with a printed circuit board ("PCB"), and which is designed for containing (inside a space circumscribed or defined by the antenna electrical turns) a transmitter coupled to and operating with the helix antenna. In one aspect of the invention, a middle part or section of the helix antenna may be embedded in a PCB. According to this aspect, the helix antenna structure may be a three-part helix antenna that may include: two, separate, parts where each part is or includes a helical conductor, and a third, middle, part or section that is interposed between the other two parts and electrically and functionally connected to the two helical conductors. The middle part or section of the helix antenna structure may include a multilayered PCB (or one layer) that includes one or more PCB conductive traces as the antenna's middle (conductive) turns, and also includes "bridging" conductive sections (e.g., PCB vias or flexible PCB traces) that electrically connect ('bridge') PCB traces in different PCB layers. A transmitter operating with the helix antenna may be mounted on the PCB such that the transmitter is completely surrounded by the helix antenna, and, in addition, such that the transmitter is electrically connected to the mid-section of the helix antenna by two antenna feeding lines which are orthogonal to a longitudinal axis of the helix antenna.

The helix antenna structure may include, according to some embodiments, a first helical conductor having a number n1 of turns (n1≥1) disposed along a longitudinal axis of said first helical conductor, a second helical conductor having a number n2 of turns (n2≥1) disposed along a longitudinal axis of the second helical conductor, and a layered PCB having a longitudinal axis. The circuit board may include a number p of circuit board layers L1, L2, . . . , Lp (p≥1) that are orderly stacked along the longitudinal axis of the circuit board. The circuit board may further include an antenna's third conductor that includes, or is made of, a number n3 of turns (1≤n3≤p+1). Each turn of the third conductor may be or include an electrically conductive trace that is disposed on, or in, a dielectric layer of a circuit board layer Li. Each conductive trace may be electrically connected to a subsequent conductive trace through a circuit via, or a blind (buried) via, in the circuit board layer Li that is interposed between one conductive trace and a subsequent, or next (e.g., adjacent) conductive trace. ("Subsequent conductive trace"—a second electrical trace that is disposed on the opposite side of a same dielectric layer on which a first conductive trace is disposed, or a second electrical trace that is disposed on a next (e.g. adjacent) dielectric layer of the ordered circuit board layers.)

The first helical conductor may include a connection end that may be mounted to, and be in electrical connection with, a conductive trace by, for example, a first mounting member, and the second helical conductor may include a connection end that may be mounted to, and be in electrical connection with, another conductive trace via, for example, a second mounting member. The circuit board may be structurally (and functionally) interposed between the first helical conductor and the second helical conductor such that the longitudinal axis of the first helical conductor, the longitudinal axis of the second helical conductor and the longitudinal axis of the circuit board may coincide.

The helix antenna structure may further include a first antenna feeding point that may be disposed, or positioned, on a first side of the circuit board, and a second antenna feeding point that may be disposed, or positioned, on a second side of circuit board. The first antenna feeding point and the second antenna feeding point may respectively coincide with, or they may be, the first mounting member and the second mounting member. The first antenna feeding point may be a connection point connecting the first helical conductor and the third conductor, and the second antenna feeding point may be a connection point connecting the third conductor and the second helical conductor.

Any one of the two antenna feeding points may reside inside the circuit board, for example inside one of the dielectric layers of the circuit board or "sandwiched" between two adjacent dielectric layers of the circuit board. In general, the two antenna feeding points on the helix antenna may reside anywhere between the connection end of the first helical conductor (the point where the first helical conductor connects to the antenna's third conductor) and the connection end of the second helical conductor (the point where the second helical conductor connects to the antenna's third conductor). The exact size, shape and location of the two antenna feeding points, and the way they are connected to the transmitter, may be selected such that the performance of the helix antenna is optimized, for example in terms of antenna impedance, transmitter's output power, obtaining circular polarization, minimizing radiation nulls in the antenna's radiation pattern, etc. For example, to facilitate these properties of the helix antenna (and transmission in general), and to optimize the performance of the helix antenna, the antenna's two feeding lines, which are two PCB conductive traces connected to the transmitter's output, in one embodiment have to traverse the antenna's longitudinal axis at an angle of ninety degrees. That is, for optimal performance of the helix antenna the antenna's two feeding lines have to, in one embodiment, lie in a plane that is perpendicular to the longitudinal axis of the helix antenna.

The circuit board may further include a transmitter that may include a first output terminal and a second output terminal that are respectively electrically connected to the first antenna feeding point and to the second antenna feeding point via an electrically conductive trace and through a via and/or blind via. The second output terminal of the transmitter may be electrically connected to the second antenna feeding point via, or using, a via and/or a blind (buried) via. The circuit board may include a through hole that may pass in or through the circuit board layers L1, L2, . . . , Lp, and the second output terminal of the transmitter may be electrically connected to the second antenna feeding point via, or using, the through hole. The transmitter may be off center with respect to the longitudinal axis of the circuit board. The circuit board may include an RF power amplifier as the transmitter. The transmitter may also be a power amplifier.

The electrically conductive traces forming the n3 turns of the third conductor may be flat and be perpendicular to longitudinal axis. Each turn, or selected turns, of the n3−1 turns of the third conductor may further include a via. The circuit board may be circular, with a diameter D1, where, for example, D1≤15 millimeters.

The first helical conductor, the second helical conductor and the third conductor may be circular with a diameter D2 (where D2≤D1) and they may satisfy the 'polarization' condition $C=\sqrt{2S\lambda}$, where, $C=\pi D2$=circumference of turns (D2=diameter of turns);
S=spacing between turns (similar to a screw pitch); and
λ=wavelength of used RF radiation.

Each of circuit board layers L1, L2, . . . , Lp may have a width, W, that may be equal to S, or may be within the range S±5%. By way of example (e.g., when used in in-vivo devices; e.g., in swallowable capsules), the diameter, D2, of the antenna turns may be D2=9.5 millimeters (or approximately 9.5 mm), the wavelength may be λ=69 centimeters (which corresponds to a radio frequency of 434 MHz) (or approximately 69 mm), and the turn spacing may be S=0.635 millimeters (or approximately 0.635 mm).

The circuit board including the helix antenna, or part thereof, may include only one circuit board layer (in which case p=1). The number of turns may be as follow: n1≥1, n2≥1 and n3≥1.

The first mounting member and the second mounting member may, respectively, may be (an integral) part, or be an extension, of the first helical conductor and the second helical conductor.

Alternatively, the first mounting member and the second mounting member may be mounted on, or be an integral part of, the circuit board itself. The circuit board may be manufactured using, for example, a printing circuit board technology, or any other technology. The type of helix antenna structure according to this aspect can be regarded as a PCB mid-section based helix antenna structure, or as a three-part helix antenna, or "TPHA" (three-part helix antenna) for short.

In another aspect of the invention, the entire helix antenna may be completely embedded (e.g., completely mounted on or in, reside or printed on, or 'built' into or formed in) a multilayered PCB. There is disclosed, according to this aspect, a helix antenna that is fully embedded in a PCB structure, such that all of the helix antenna's turns are PCB conductive traces. This type of helix antenna structure can be regarded as a full PCB helix antenna structure ("FPHA").

A transmitter operating with the FPHA may be mounted on the PCB such that the transmitter is completely contained by the FPHA, and, in addition, such that the transmitter is electrically connected to the FPHA by two antenna feeding lines that are orthogonal to a longitudinal axis of the helix antenna.

There is also disclosed herein an in-vivo device that includes, or incorporates, the helix antenna structure, though other devices may also benefit from the helix antenna structure. In addition to the helix antenna, the in-vivo device may include a controller, a battery, a sensor circuit for sensing a physiological parameter (e.g., temperature, pressure, pH, etc.) and/or an image sensor, a transducer, a light source and a transmitter for transmitting sensory data by using the helix antenna.

The PCB on which the helix antenna is mounted (partly or completely) may be part of, or a sub-circuit in, a PCB that may additionally include, for example, a sensor circuit, a transducer, a clock generator, a memory, a light source and a controller. The in-vivo device may be selected from the group consisting of a swallowable device (e.g., a swallowable imaging capsule used, for example, in capsule endoscopy) and an implantable device (e.g., a heart pacemaker).

In another aspect of the invention, a helix antenna structure may be a multilayered PCB that may include a plurality of loop antennas and a plurality of PCB layers (e.g., six PCB layers). Each PCB layer may include a peripheral loop antenna, and each two adjacent loop antennas may be electrically connected by a connection bridge functioning as a monopole antenna. A selected one of the PCB layers may be configured to physically and electrically accommodate a transmitter inside a peripheral loop antenna of, related to, or mounted in or on the selected PCB layer. The selected PCB layer may include a first antenna feeding line. The first antenna feeding line may electrically connect the peripheral loop antenna of the selected PCB layer to a first output terminal of the transmitter. (The first antenna feeding line may split off from the peripheral loop antenna and be configured to be connected, or connectable, to a first output terminal of the transmitter.)

The selected printed circuit board layer may also include a second antenna feeding line. The second antenna feeding line may electrically connect a second peripheral loop antenna to a second output terminal of the transmitter. (The second antenna feeding line may split off from the second peripheral loop antenna and be configured to be connected, or connectable, to a second output terminal of the transmitter.) The second antenna feeding line may be partly disposed on the selected PCB layer and partly disposed on a non-selected PCB layer. Alternatively, the second antenna feeding line may be entirely disposed on a non-selected PCB, and be connected to the transmitter through a PCB via.

The PCB may be foldable such that, in the folded state, the plurality of PCB layers are lengthwise stacked along a longitudinal axis and ordered from a first PCB layer including a first loop antenna to a last PCB layer comprising a last loop antenna, and such that the first antenna feeding line and the second antenna feeding line lie in a plane that is perpendicular to the longitudinal axis. The selected PCB layer may be lengthwise located in a middle section of the multilayered PCB.

The helix antenna may additionally include a first helical conductor that may be electrically connected to the first loop antenna in the ordered stacked PCB layers, and a second helical conductor that may be electrically connected to the last loop antenna in the ordered stacked PCB layers.

The helix antenna may also include an antenna extension (e.g., a 'tail'). The antenna's extension may be electrically connected (e.g., directly or through a PCB via) to the last peripheral loop antenna in the ordered stack of the PCB layers, and it may axially extend (e.g., in parallel to the longitudinal axis), away from the extending away from the stack of the PCB layers and away from the transmitter. The peripheral loop antennas may be circular and have a diameter D2, and the peripheral loop antennas may satisfy the circular polarization condition $C=\sqrt{2S\lambda}$, where C ($C=\pi D2$) is the circumference of the turns, S is the spacing between loop antennas, and λ is the wavelength of the radio frequency for which the helix antenna is designed.

Each circuit board layer may have a thickness W that may be equal to S (in order enable operating the antenna in the circular polarization mode), or thickness W may be within the range S±5%. The diameter, D2, of the loop antennas may be, for example, 9.5 millimeters, to make it suitable for insertion into a swallowable in-vivo capsule. The wavelength, λ, of the RF used may be, for example, 69 centimeter (which corresponds to a frequency of 434.78 MHz), and the spacing, S, between loop antennas may be, for example, 0.635 millimeters.

In another aspect of the invention a PCB for a helix antenna structure may include a plurality of PCB layers. Each PCB layer may include at least one peripheral loop antenna, and each two adjacent loop antennas may be electrically connected by a connection bridge functioning as a monopole antenna. A selected one of the PCB layers may be configured to physically and electrically accommodate a transmitter inside a peripheral loop antenna of, related to, or disposed in or on the selected printed circuit board layer. The PCB may further include a first antenna feeding line that may be disposed on the selected PCB layer and electrically connected to, or be split from, the loop antenna of the selected PCB layer and configured to be electrically connected, or connectable, to a first output terminal of the transmitter. The PCB may further include a second antenna feeding line that is electrically connected to, or be split from, another loop antenna and configured to be electrically connected, or connectable, to a second output terminal of the transmitter.

The second antenna feeding line may be partly disposed on the selected printed circuit board layer and partly disposed on a non-selected printed circuit board layer, or it may be entirely disposed on a non-selected printed circuit board layer.

The PCB may be foldable such that, in the folded state, the plurality of PCB layers are lengthwise stacked along a longitudinal axis and ordered from a first PCB layer that includes a first loop antenna to a last PCB layer that includes a last loop antenna. The plurality of PCB layers are lengthwise stacked such that the first antenna feeding line and the second antenna feeding line lie in a plane perpendicular to the longitudinal axis. The selected PCB layer may be lengthwise located in a middle section of the multilayered PCB. The PCB may further include an antenna extension (e.g., a 'tail') that is electrically connected to the last loop antenna and axially extending away from the stack of the PCB layers and away from the loop antennas and from the transmitter.

In another aspect of the invention, an in-vivo device may include a helix antenna that is structured in accordance with any of the embodiments or aspects disclosed herein.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 9A-9B schematically show a one-circuit board layer of a helix antenna for a PCB mid-section based helix antenna according to an example embodiment;

FIG. 15 shows example helix antenna turns for a FPHA according to an example embodiment;

FIG. 16 shows the helix antenna turns of FIG. 15 integrated into a multilayered PCB according to an example embodiment;

FIGS. 18A and 18B depict an example spread out PCB for a FPHA according to another example embodiment; and FIGS. 19A and 19B depict an optical head of an in-vivo device that includes a FPHA similar to the FPHA of FIGS. 17A-17B and FIGS. 18A-18B.

DETAILED DESCRIPTION OF THE INVENTION

The description that follows provides various details of exemplary embodiments. However, this description is not intended to limit the scope of the claims but, instead, to explain various principles of the invention and the manner of practicing it.

In the following description, various aspects of the invention will be described. For purposes of explanation, specific configurations and details are set forth in order to facilitate a thorough understanding of the invention. However, it will also be apparent to one skilled in the art that the invention may be practiced without the specific details presented herein. Furthermore, well-known features may be omitted or simplified in order not to obscure the invention.

Circular polarization of an electromagnetic wave is a polarization in which the electric field of the passing wave does not change strength but only changes direction in a rotary manner. In radio transmission, circular polarization is often used when the relative orientation of the transmitting and receiving antennas cannot be easily controlled, or when the polarization of the signal may change.

A helix antenna can be operated in two main radiation modes—normal mode and axial mode. For a very small helix antenna (for a helical antenna with a size that is much smaller than the used radio frequency ("RF") wavelength ($\lambda$), the maximum RF radiation occurs in the plane perpendicular to the axis of the helix antenna. This mode of operation is referred to as the "normal mode". In general, the RF radiation field produced by the normal-mode helix antenna ("NMHA") in the normal mode is elliptically polarized in all directions though, under particular conditions, the RF radiation field can be circularly polarized. Because of its small size compared to the RF wavelength, the NMHA is generally regarded as having low efficiency and narrow bandwidth.

Figure 1:
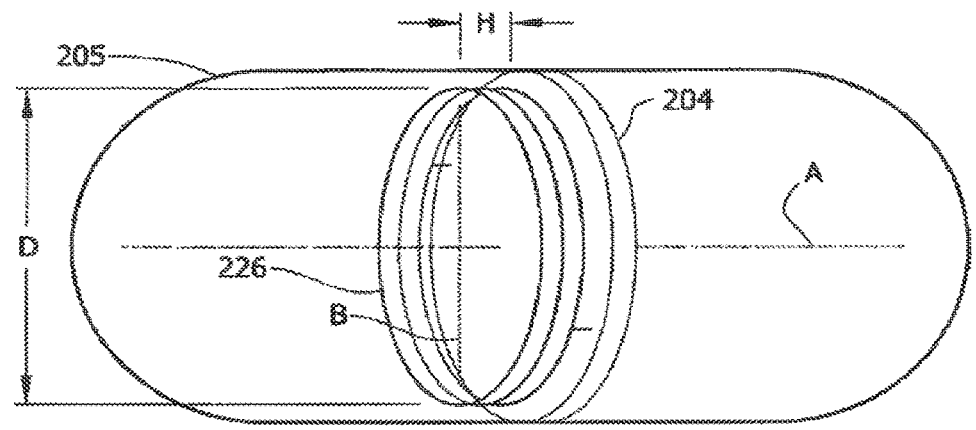
FIGS. 1-7B (prior art) show example conventional antennas.
Figure 2:
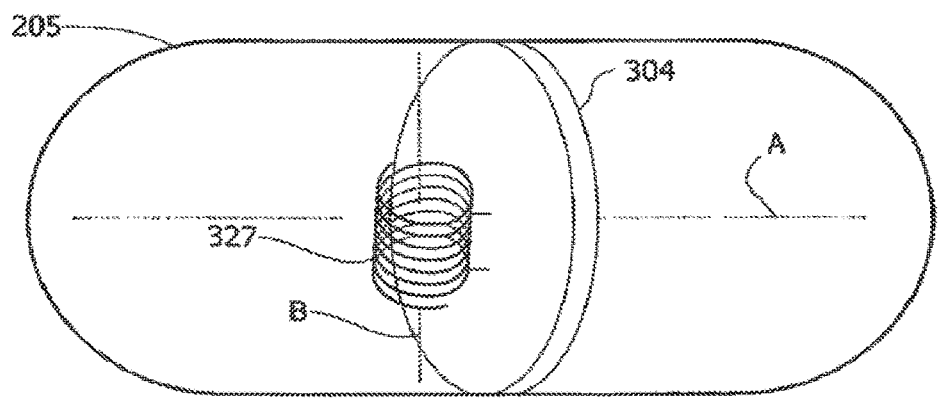
Figure 3B:
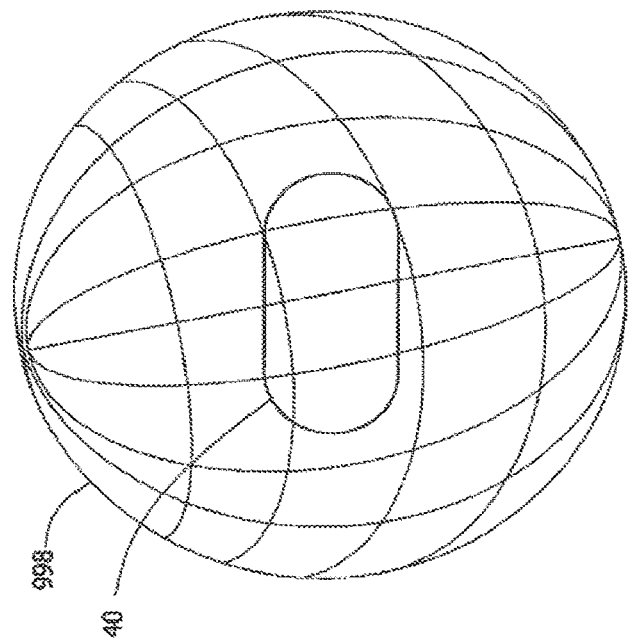
Figure 3A:
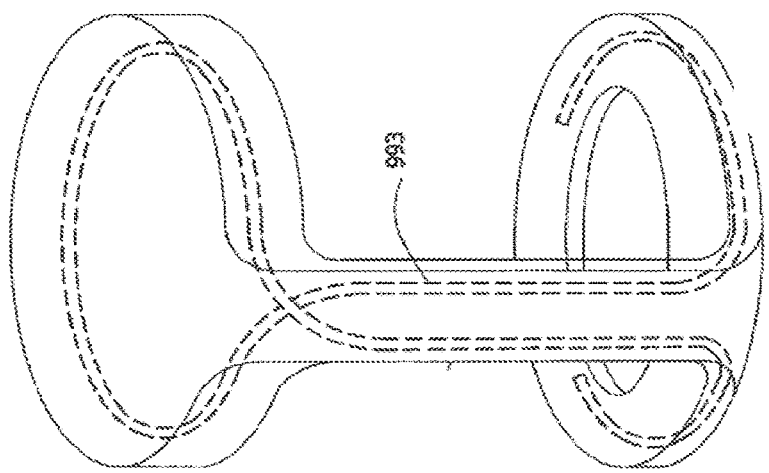
Figure 4B:
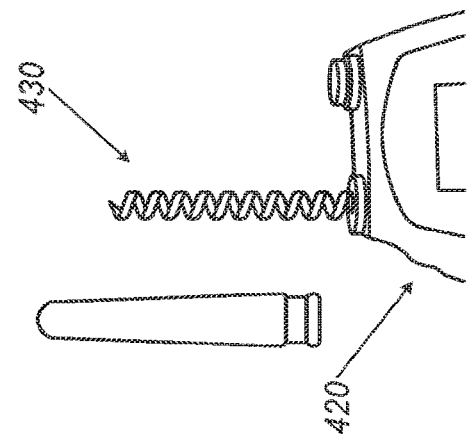
Figure 4A:
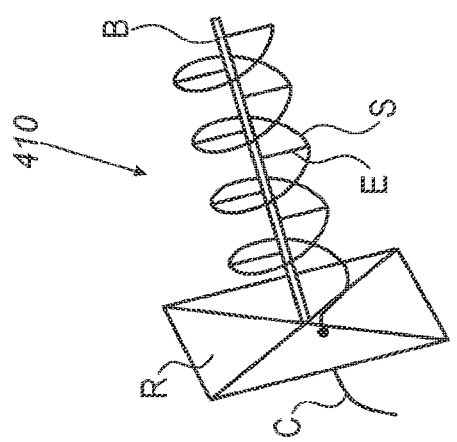
Figure 6:
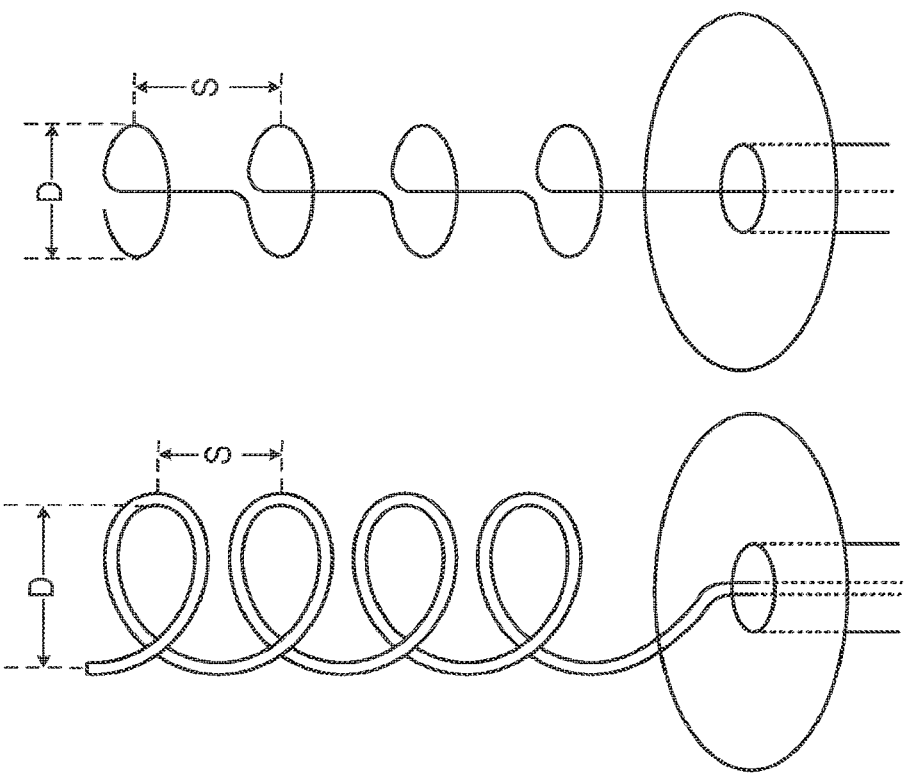
Figure 5:
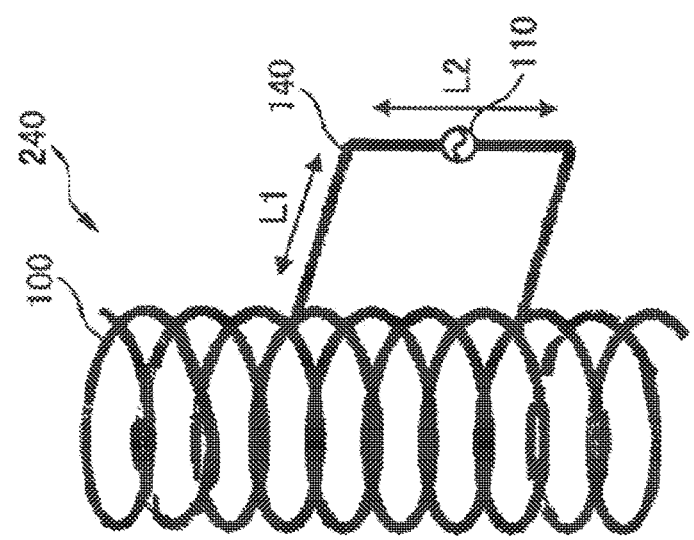
Figure 7B:
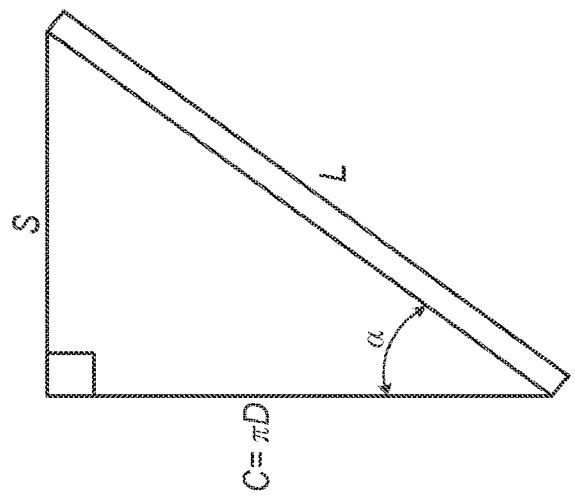
Figure 7A:
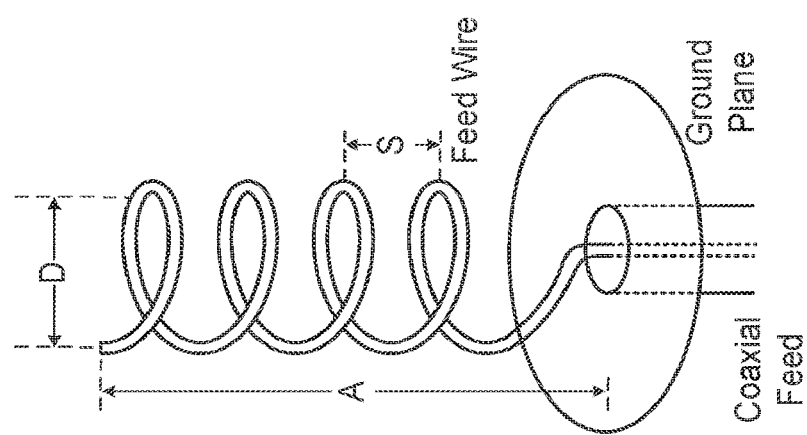

A NMHA can be modeled as a superposition of monopoles and loop antennas, as for example shown in FIG. 6. The monopole fields and the loop fields are mutually perpendicular and have a 90 degree phase shift between them. A NMHA that satisfies the condition $2S\lambda=n^2D^2$ (see FIGS. 7A-7B)) can, therefore, transmit a signal using circular polarization.

When the circumference of a helix antenna is near the RF wavelength ($\lambda$) of operation, the helix antenna operates in the axial mode. This is a non-resonant traveling wave mode in which instead of standing waves, the current and voltage waves travel in one direction, up the helix. Under particular conditions, a helix antenna operating in the axial mode can also radiates RF waves with circular polarization along the antenna's axis, off the ends of the antenna. (Since in a directional antenna only radiation in one direction is wanted, the other end of the helix antenna is terminated in a flat metal sheet or screen reflector (see ground plane in FIG. 7A) to reflect the waves forward.) However, as opposed to the relatively small NMHA, axial mode helix antennas ("AM-HAs") cannot be used in small devices such as swallowable devices (and other in-vivo devices), implantable devices, etc., due to their relatively large size. ('Large size'—comparing to the wavelength of the communication RF that the antenna is designed to operate with, which, in a case of a swallowable in-vivo device (for example), may be in the approximate range of 400 megahertz (MHz) to 450 MHz.

The circuit board based helix antenna subject of the present invention has at least the following advantages: (1) its size can be made very small (e.g., small enough to be incorporated in an in-vivo device; e.g., in an in-vivo imaging device, and in an implantable device; e.g., heart pacemaker), (2) the helix antenna's impedance can be raised to match an RF power amplifier (PA), (3) using a PA enables managing and controlling of the used transmission power, for example as a function of the quality of the communication channel, and (4) the communication performance of the conventional in-vivo device may be obtained by using lowered transmission power, which is a major advantage when the energy source powering the in-vivo device is a non-rechargeable battery. (Alternatively, the communication performance of an in-vivo device that uses the novel helix antenna may be improved by slightly increasing the transmission power, for example when electromagnetic interferences get stronger.)

Figure 8:
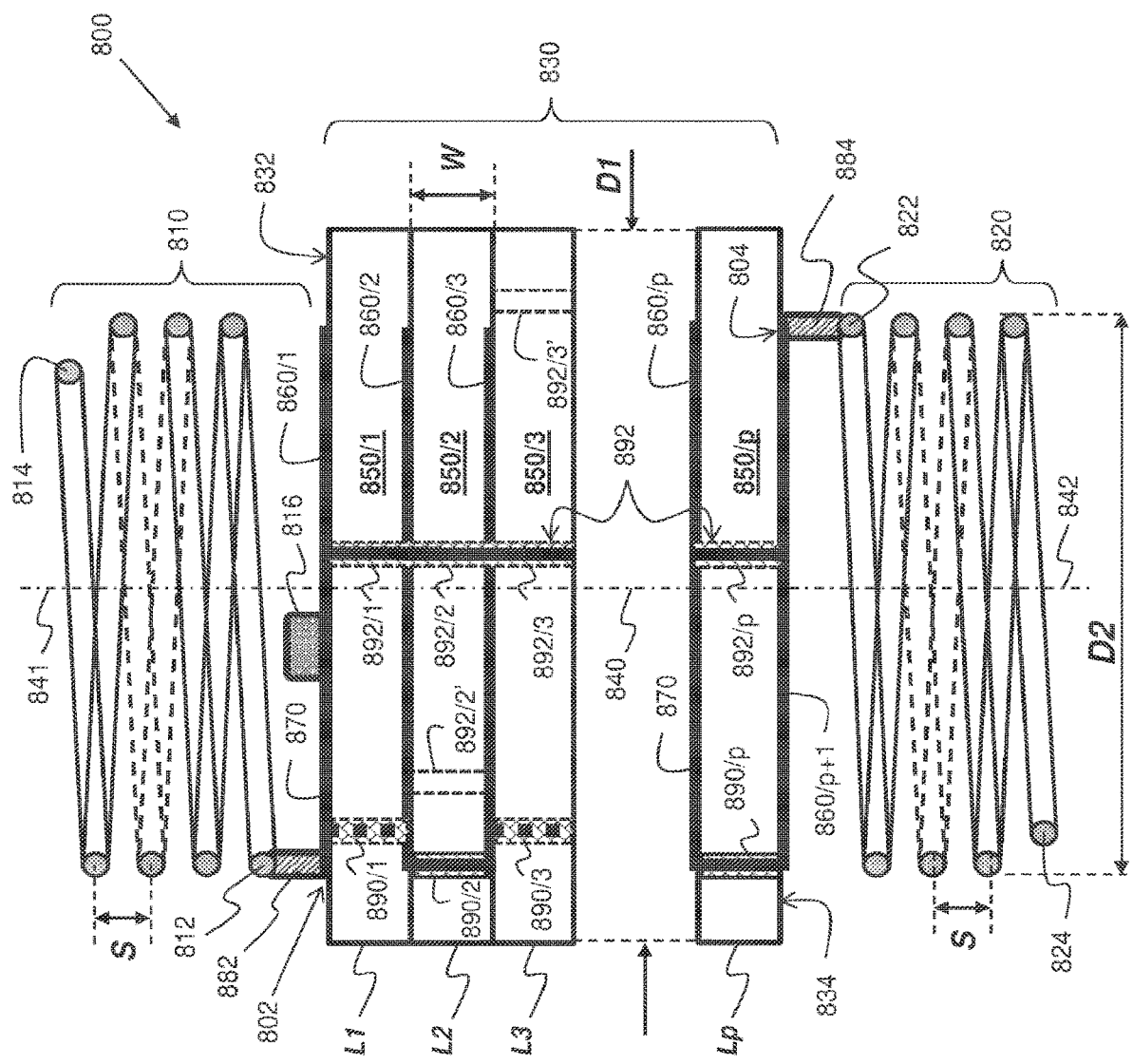
FIG. 8 schematically shows a general structure of a TPHA (three-part helix antenna) according to an example embodiment.

As described herein, NMHAs can be modeled as a superposition of monopoles and loop antennas (FIG. 6). The helix antenna structure of the present invention makes use of the helix antenna model in the sense that, in the embodiment of FIG. 8, for example, a middle section of the antenna (e.g., antenna conductor 870, FIG. 8) is structured, formed, incorporated or embedded in a circuit board (e.g., a PCB) such that it structurally resembles the model. Namely, as in the model, conductor 870 (FIG. 8) includes peripheral loop antennas, e.g., in the form of electrical (PCB) traces 860, in multilayered PCB 830, FIG. 8), and straight lines or bridges (e.g., in the form of, for example, PCB vias 890) that are perpendicular to the planes of the loop antennas, connect the various loop antennas (860) and function as monopole antennas. (A peripheral loop antenna may be, for example, a PCB trace that is part of an antenna and may lie at, or adjacent to, the periphery of a PCB layer.) In other words, the helix antenna subject of the present invention may include two end helical conductors (e.g., helical conductors 810, 820, FIG. 8) and a middle conductor (e.g., 870, FIG. 8), which is interposed (structurally and functionally) between the two end helical sections, whose structure resembles the model of the helix antenna. (Helical conductors 810 and 820 may be optional. A helix antenna structure that does not include helical conductors is shown in FIGS. 15 through 19B, which are described below.) Embedding a middle conductor, or section, of a helix antenna in a circuit board in the ways described herein has many advantages, some of which are described herein below (e.g., improved impedance matching, increased impedance relative to conventional NMHAs, elimination of null areas in the antenna's radiation pattern, flexibility in antenna design—traces layout and location of vias/blind vias can be determined per antenna's required properties, etc.).

An aspect of the invention is that the exact location of the two antenna feeding points, and the way they are connected to a transmitter, are selected such that the performance of the helix antenna is optimized, for example in terms of antenna impedance, transmitter's output power, obtaining circular polarization, minimizing nulls in the antenna's radiation pattern, etc. For example, to facilitate these properties of the helix antenna (to facilitate optimal performance of the antenna), the antenna's two feeding lines, which are two PCB traces connected to the transmitter's output, lie in a plane that is perpendicular to the antenna's longitudinal axis. Mounting the antenna feeding lines this way, in, or as part of, a PCB, mitigates the problem of longitudinal, or axial, RF transmission by the antenna's feeding lines, because, by mounting the transmitter inside the antenna structure (on a PCB layer), the length of the bridging conductor (e.g., PCB via), which connects an antenna feeding line to the transmitter or to a PCB trace on the transmitter's PCB layer that is connected to the transmitter, can be minimized so as to minimize the unwanted, or deviant, RF radiation from this antenna conductor.

Referring again to FIG. 8, a helix antenna structure 800 is schematically illustrated according to an example embodiment. Helix antenna structure 800 may include a first helical conductor 810 having a number n1 of turns (n1≥1) that may be placed or disposed along a longitudinal axis 841 of first helical conductor 810, a second helical conductor 820 having a number n2 of turns (n2≥1) that may be placed or disposed along a longitudinal axis 842 of second helical conductor 820, and a multilayered PCB 830 having a longitudinal axis 840. Circuit board 830 may include a number p of circuit board layers, designated as layers L1, L2, . . . , Lp (p≥1), that are orderly stacked along longitudinal axis 840 of PCB structure 830. Printed circuit board 830 may also include a third conductor 870 having a number n3 of turns (2≤n3≤p+1). Each turn of third conductor 870 may include an electrically conductive trace 860/$i$ that is placed or disposed on, or in, a dielectric layer 850/$i$ of a circuit board layer Li, and each conductive trace 860/$i$ may be electrically connected to a subsequent conductive trace 860/$i$+1 through a via 890/$i$ (e.g., a "trace via") in the circuit board layer Li that is interposed between conductive trace 860/$i$ and the subsequent conductive trace 860/$i$+1. ("Subsequent conductive trace" means a conductive trace that may be formed in or on the other (opposite) side of the same dielectric layer 850/*i*, or a conductive trace that may be formed in or on an adjacent dielectric layer 850/*i*+1.)

Helical conductor 810 may include a connection end 812 that may be mounted to, and may be in electrical connection with, conductive trace 860/1 using a first mounting member 882. Helical conductor 810 also may include a termination end 814 that is neither connected to anything electrically nor mechanically. Helical conductor 820 may include a connection end 822 that may be mounted to, and may be in electrical connection with, conductive trace 860/*p*+1 via a second mounting member 884. Helical conductor 820 also includes a termination end 824 that is neither connected to anything electrically nor mechanically. Mounting member 882 and mounting member 884 may, respectively, be part, or may be an extension, of helical conductor 810 and helical conductor 820.

Multilayered PCB 830 may be structurally (and functionally) interposed between helical conductor 810 and helical conductor 820 such that the axis of helical conductor 810, the axis of helical conductor 820 and axis 840 of multilayered PCB 830 coincide (e.g. occupy the same line and orientation). Mounting member 882 may be, for example, a conductive pin that is mounted on (e.g., protrude from or be flatly mounted on) circuit board layer L1 and electrically connected to conductive trace 860/1, and connection end 812 of helical conductor 810 may be mechanically and electrically connected to mounting member 882, for example, by being soldered to mounting member 882. Similarly, mounting member 884 may be, for example, a conductive pin that is mounted on (e.g., protrude from or be flatly mounted on) circuit board layer Lp and electrically connected to conductive trace 860/*p*+1, and connection end 822 of helical conductor 820 may be mechanically and electrically connected to mounting member 884, for example, by being soldered to mounting member 884.

Small, or compact, implantable, or in-vivo, devices (e.g., swallowable capsules) have only small space for accommodating a communication antenna. Therefore, the size of an antenna that is to be embedded in such small devices has roughly to be in the order of millimeters, and, when a helix antenna is to be used, the number of antenna turns is limited to just a few coil turns (e.g., less than three turns). Therefore, a helix antenna that is designed under the strict space constraints of an in-vivo device (or implantable device) may have a very low impedance, Z (e.g., Z=1-4 ohms). An antenna having such a low impedance cannot efficiently interoperate with an RF power transmitter, for example because of increased power loss. To mitigate this problem, helix antenna structure 800 is structured as an autotransformer with a tap that steps up the antenna's impedance in order to increase the antenna's impedance so as to make the antenna suitable for operation with an RF power transmitter. To this effect, helix antenna structure 800 may also include a first antenna feeding ("tapping") point 802 that is disposed on a first side 832 (in FIG. 8 the 'top' side) of PCB structure 830, and a second antenna feeding (tapping) point 804 that is disposed on a second side 834 (the other, or 'bottom', side) of PCB structure 830, opposite the first side (832) of circuit board 830. Antenna feeding (tapping) points 802 and 804 may, respectively, overlap (or be adjacent to) mounting member 882 and mounting member 884. Feeding point 802 may be a connection point electrically connecting helical conductor 810 and conductor 870, and antenna feeding point 804 may be a connection point electrically connecting conductor 870 and helical conductor 820. (Antenna feeding points 802 and 804 are points on the helix antenna via which a transceiver transmits or receives RF signals.)

Any one of the two antenna feeding points 802 and 804 may reside on or in PCB structure 830, for example inside one of the dielectric layers (e.g., dielectric layer 850/2) of PCB structure 830, or "sandwiched" between two adjacent dielectric layers of the circuit board (for example between dielectric layers 850/2 and 850/3). In general, the two antenna feeding points on helix antenna 800 may reside anywhere between connection end 812 of helical conductor 810 (the point where helical conductor 810 connects to the antenna's third conductor 870) and connection end 822 of helical conductor 820 (the point where helical conductor 820 connects to antenna's third conductor 870). The exact location of the two antenna feeding points (and antenna feeding lines) may be selected such that the performance of the helix antenna is optimized, for example, in terms of antenna impedance and/or transmitter's output power and/or generation of circular polarization radiation and/or minimizing radiation nulls in the antenna's radiation pattern, etc.

Helical antenna structure 800 (e.g., circuit board 830) may also include an RF transmitter 816 and a PCB via 892 that may pass through all the circuit board layers L1, L2, . . . , Lp. RF power transmitter 816 may be mounted on the first side 832 of circuit board 830 and include a first output terminal that is electrically connected to antenna feeding point 802, and a second output terminal that is connected to antenna feeding point 804. The second output terminal of RF power transmitter 816 may be electrically connected to antenna feeding point 804 by or through via 892. The second output terminal of transmitter 816 may be electrically connected to antenna feeding point 804 by using a PCB via and/or a blind (buried) via. Transmitter 816 may also be a power amplifier.

Via 892 includes multiple vias (e.g., vias 892/1, 892/2, . . . , 892/p), one or more vias per PCB layer of circuit board 830, that are all aligned to form one continuous via path. Alternatively, PCB structure 830 may include multiple vias, one or more vias per layer of PCB structure 830, that are laterally (with respect to the surface of the layers) displaced (that is, at least some of the vias do not align) and are interconnected by conducting traces. For example, vias 892/2 and 892/3 may be displaced with respect to the other vias 892 (and optionally with respect to one another) and interconnected to the other vias (buried and unburied) by electrical (conducting) traces. (The displaced vias 892/2 and 892/3 are respectively shown at locations 892/2' and 892/3'.)

RF power transmitter 816 may be positioned anywhere on PCB structure 830 (e.g., it may be positioned in the center of circuit board 830 or off center with respect to longitudinal axis 840 of circuit board 830).

While the n1 and n2 turns of conductors 810 and 820, respectively, are helical, with each coil turn individually forming a three-dimensional curve, the electrically conductive traces 860 forming the n3 turns of conductor 870 may be flat and perpendicular to longitudinal axis 840 of PCB structure 830. In some embodiments, the PCB structure 830 may include one layer (i.e., p=1). The values of n1, n2 and n3 may be equal to or greater than one for any number of circuit board layers; namely, for any value of p.

In some embodiments, each turn of n3−1 turns of the third conductor 870 may include only a conductive trace or a via 890/*i* in addition to a conducting trace. In some embodiments, PCB structure 830 is a circular or cylindrical object having a diameter D1 (for example D≤15 millimeters). In some embodiments, helical conductor 810, helical conductor 820, and conductor 870 are circular with a diameter D2 (where D2<D1). In order for helix antenna 800 to operate in the circular polarization mode the condition $C=\sqrt{2S\lambda}$ has to be satisfied where C (=πD2) is the circumference of turns (D2 is the diameter of the turns), S is a length-wise spacing between each two turns and λ, is the wavelength of the used RF radiation. PCB vias 890 and mounting members 882 and 884 serve as monopole antenna elements, per the helix antenna model of FIG. 6.

In some embodiments, each layer of circuit board layers L1, L2, . . . , Lp has a thickness W that may be equal to S, or may be within the range of, for example, S±5%. By way of example, D2=9.5 millimeters, λ=69 centimeters (corresponding to a radio frequency of 434 MHz), and S=W=0.635 millimeters. In another example, D may be approximately 9.5 millimeters, λ may be approximately 69 centimeters (corresponding to a radio frequency of approximately 434 MHz), and S may be approximately W=0.635 millimeters, where 'approximately' is, for example, ±5%. Other parameters and dimensions may be used. (The example values of D2, S and W used above satisfy the circular polarization mode condition C=√2Sλ)

Transmitter 816 may be mounted on a selected one of the PCB layers (e.g., on PCB layer L1), which is configured to physically and electrically accommodate the transmitter inside the peripheral loop antenna 860/1 related to the selected PCB layer L1. ('Accommodate'—having a physical space on the PCB layer that is allotted for mounting the transmitter, and including all the PCB conductive traces required to operate the transmitter. Transmitter 816 may be mounted on a different PCB layer; that is, different PCB layers may accommodate the transmitter.) The selected PCB layer (e.g., L1) may include a first antenna feeding line (e.g., 870) that is electrically connected to, or split off from, the loop antenna (e.g., 860/1) disposed on the selected PCB layer (e.g., layer L1) and configured to be electrically connected, or connectable, to a first output terminal of the transmitter. The selected printed circuit board layer may also include a second antenna feeding line that is electrically connected to a second loop antenna in a non-selected PCB layer, and configured to be electrically connected, or connectable, to a second output terminal of the transmitter.

FIG. 9A depicts an example circuit board 900 for a helix antenna structure according to another example embodiment. (Circuit board 900 is an example case where p=1.) Circuit board 900 includes one layer, L, and an electrically conductor 970, and has a longitudinal axis 940. (By way of example, longitudinal axis 940 coincides with the Z axis in that it occupies the same space and orientation.) Conductor 970 may include one antenna turn (e.g., one loop antenna), or two loop antennas or antenna turns, or any number of turns between one and two. By way of example, conductor 970 includes approximately one and half antenna turns. Each antenna turn of conductor 970 includes an electrically conductive trace (loop antenna) 960/i that is disposed on, or in, a different side of dielectric layer 950 of circuit board layer L. One turn of conductor 970 includes an electrically conductive trace 960/1 that is disposed on the "upper" side of layer L of circuit board 900, and the other turn of conductor 970 includes an electrically conductive trace 960/2 that is disposed on the "lower" side of layer L of circuit board 900. Conductive trace 960/1 and conductive trace 960/2 are interconnected through via 990 (a "trace via") that passes through, or in, the circuit board layer L which is interposed between conductive traces 960/1 and 960/2. Every PCB via that is connected to a loop antenna (e.g., a PCB via that connects two loop antennas, or two antenna turns) functions as a monopole antenna per the helix antenna model shown in FIG. 6.

Circuit board 900 may be configured to be structurally (and functionally) interposed between two helical conductors (e.g., helical conductors 910 and 920, see FIG. 10, for example) such that the axis of the two helical conductors and axis 940 of circuit board 900 coincide (e.g., occupy the same space and orientation). Circuit board 900 may include an "upper" mounting member 982 and a "lower" mounting member 984. Mounting member 982 may be a conductive pin that is mounted on (e.g., protrude from or be flatly mounted on) circuit board layer L and electrically connected to conductive trace 960/1, and a connection end of a first helical conductor (e.g., helical conductor 910, FIG. 9C) may be connected to mounting member 982, for example, by being soldered to mounting member 982. Similarly, mounting member 984 may be a conductive pin that is mounted on (e.g., protrude from or be flatly mounted on) circuit board layer L and electrically connected to conductive trace 960/2, and a connection end of a second helical conductor (e.g., helical conductor 920, FIG. 9D) may be connected to mounting member 984, for example, by being soldered to mounting member 984.

Circuit board 900 may also include a first antenna feeding ("tapping") point 902 that is disposed on a first (the upper) side of circuit board 900, and a second antenna feeding (tapping) point 904 that is disposed on a second (the lower, or opposite) side of circuit hoard 900. Antenna feeding (tapping) points 902 and 904 may, respectively, overlap (or be adjacent to) mounting members 982 and 984. Antenna feeding point 902 may be used as a connection point for connecting a first helical conductor 970, and antenna feeding point 904 may be uses as a connection point connecting helical conductor 970 and another helical conductor. (Antenna feeding points 902 and 904 are points on the helix antenna via which a transceiver transmits or receives RF signals.)

An RF power transmitter 916 (or a transceiver) may be mounted on the upper side of the circuit board layer L. RF power transmitter 916 may include a first output terminal that is electrically connected to a first antenna feed line (a PCB trace) 994, and a second output terminal that is electrically connected to a second antenna feed line (a PCB trace) 996. Antenna feed line 994 may be electrically connected to (the upper) antenna feeding point 902. Antenna feed line (a trace) 996 may be electrically connected to (the lower) antenna feeding point 904 through via 992 in circuit board layer L.

Antenna feeding line 994 may be electrically connected to, or split off from, loop antenna 960/1 and be configured to be electrically connected, or connectable, to a first output terminal of transmitter 916. Antenna feeding line 996 may be electrically connected to, or split off from, loop antenna 960/2 and configured to be electrically connected, or connectable, to a second output terminal of transmitter 916.

Transmitter 916 may also be, or include, a power amplifier. RF power transmitter 916 may be positioned anywhere in circuit board 900 (e.g., it may be positioned in the center of circuit board 900 or off center with respect to longitudinal axis 940 of circuit board 900). Electrically conductive traces 960/1 and 960/2 of conductor helical 970 may be flat and lie in, or define, a plane that is perpendicular to longitudinal axis 940 of circuit board 830. In some embodiments, an antenna turn (a loop antenna) of helical conductor 970 (e.g., the antenna turn including conducting trace 960/1) may also include via 990 in addition to the conducting trace.

FIG. 9B is an orientation figure showing various elements of FIG. 9A from a different perspective. Each reference numeral in FIG. 9B refers to a corresponding reference numeral and element in FIG. 9A. For example, reference numeral 916' in FIG. 9B refers to transmitter 916 in FIG. 9A, reference numeral 982' in FIG. 9B refers to mounting member 982 in FIG. 9A, reference numeral 990' in FIG. 9B refers to trace via 990 in FIG. 9A, reference numeral 992' in FIG. 9B refers to feed via 992 in FIG. 9A, reference numeral 996' in FIG. 9B refers to antenna feed line (a PCB trace) 996 in FIG. 9A, and so on.

Figure 9C:
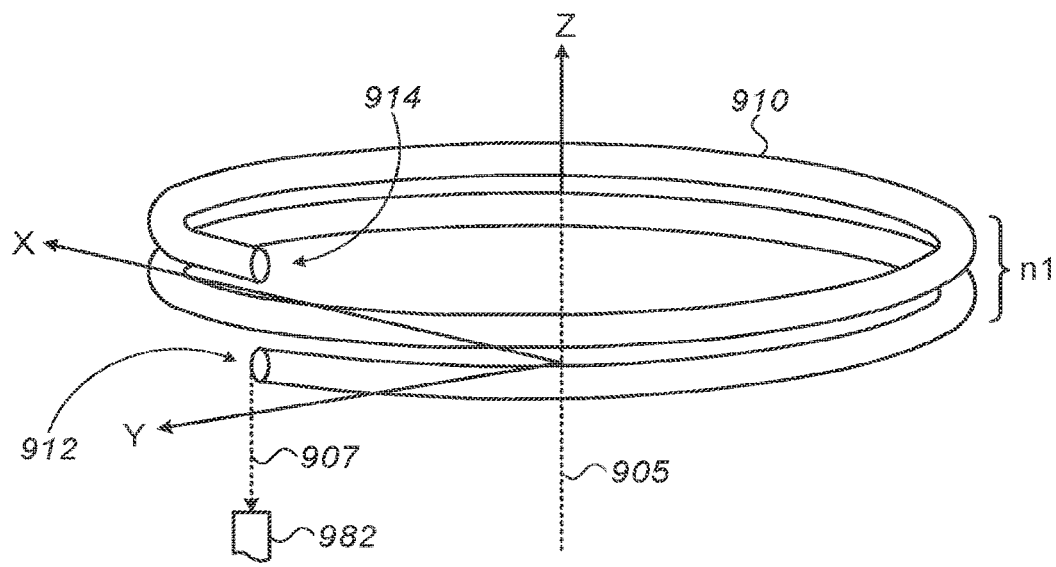
FIGS. 9C-9D depict helical conductors for PCB mid-section based helix antenna according to an example embodiment.

FIG. 9C shows a helical conductor 910 according to an example embodiment. By way of example, helical conductor 910 includes two antenna turns (n1=2) that are lengthwise disposed along a longitudinal axis 905 that, in this example, coincides with the Z-axis in that they occupy the same line and orientation. (n1 may have other values than 2.) Helical conductor 910 has a connection end 912 that may be mounted (907) to, and may be in electrical connection with a conductive trace similar to conductive trace 960/1 of FIG. 9A using a mounting member similar to mounting member 982 of FIG. 9A. Helical conductor 910 also has a termination ("free") end 914 that is neither connected to anything electrically nor mechanically.

Figure 9D:
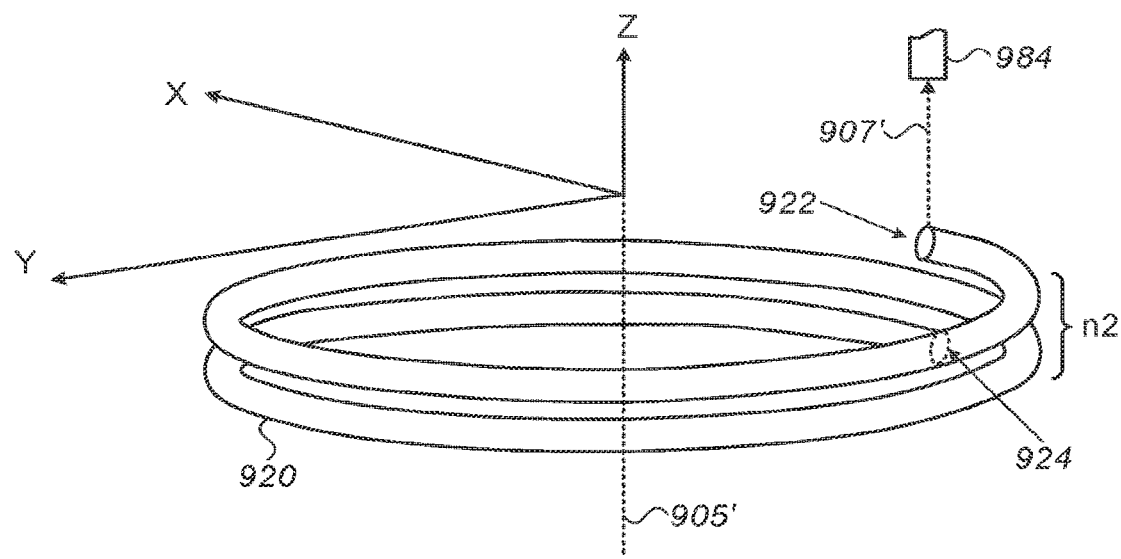

FIG. 9D shows a helical conductor 920 according to an example embodiment. By way of example, helical conductor 920 includes two antenna turns (n2=2) that are lengthwise disposed along a longitudinal axis 905' that, in this example, coincides with the Z-axis. (n2 may have other values than 2.) Helical conductor 920 has a connection end 922 that may be mounted (907') to, and may be in electrical connection with a conductive trace similar to conductive trace 960/2 of FIG. 9A using a mounting member similar to mounting member 984 of FIG. 9A. Helical conductor 920 also has a termination ("free") end 924 that is neither connected to anything electrically nor mechanically.

Figure 10:
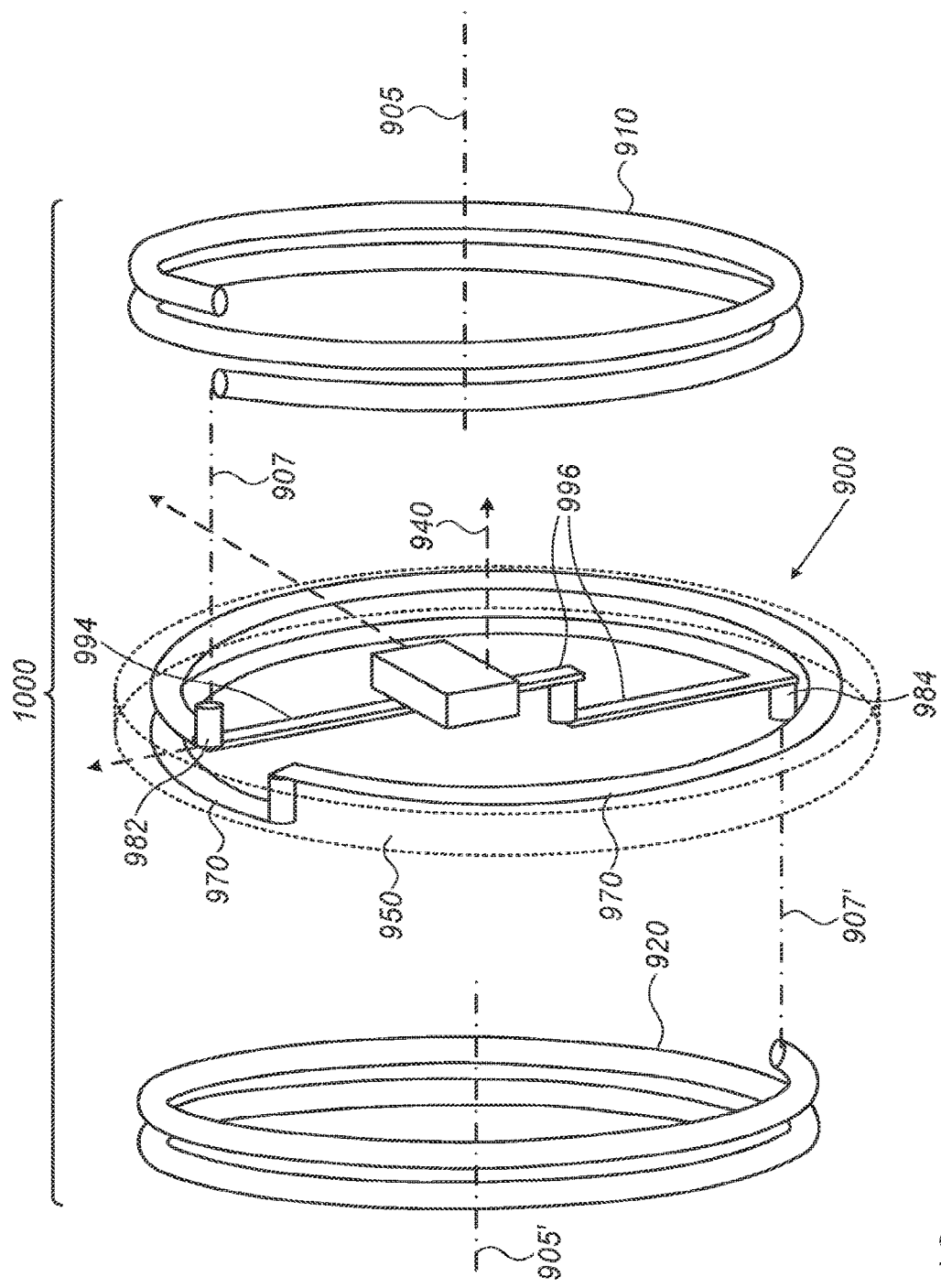
FIG. 10 depicts a disassembled helix antenna for a PCB mid-section based helix antenna according to an example embodiment.
Figure 11A:
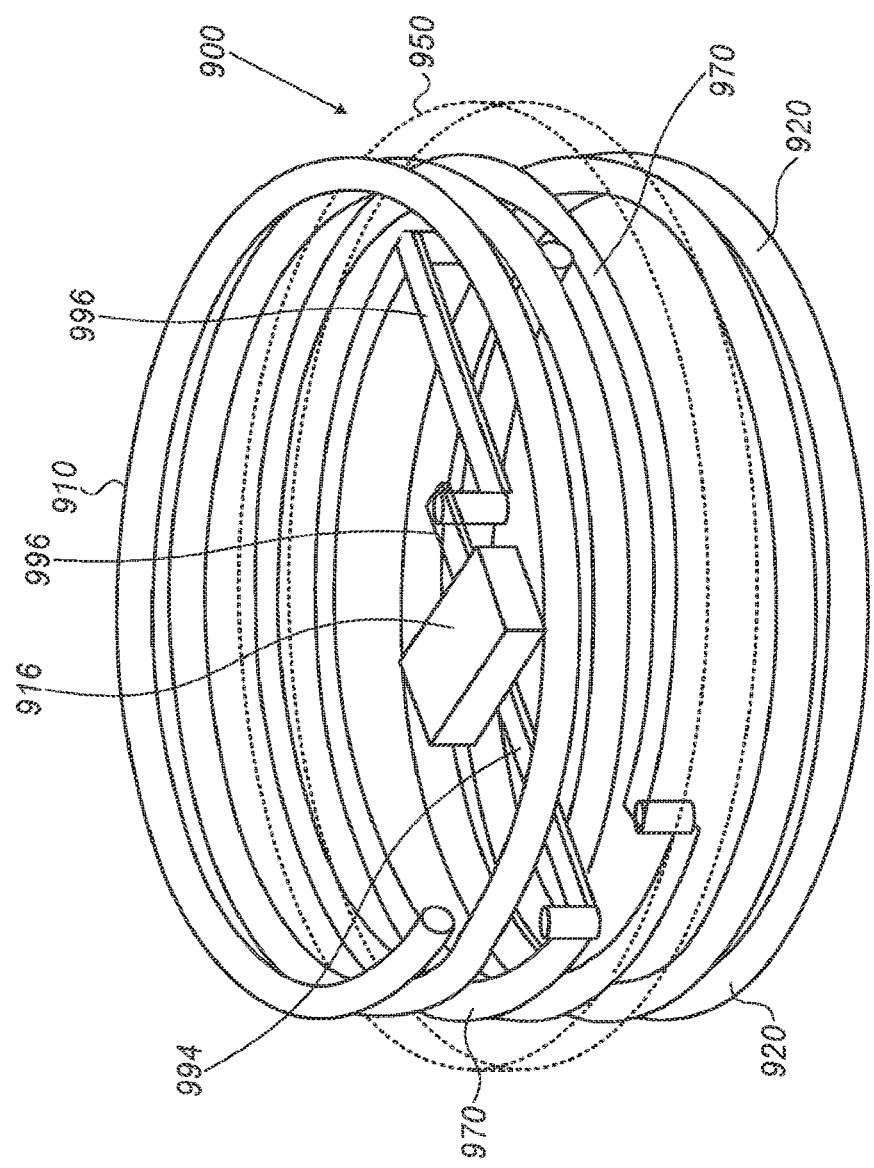
FIGS. 11A-11E depict the helix antenna structure of FIG. 10 from different perspectives.
Figure 11B:
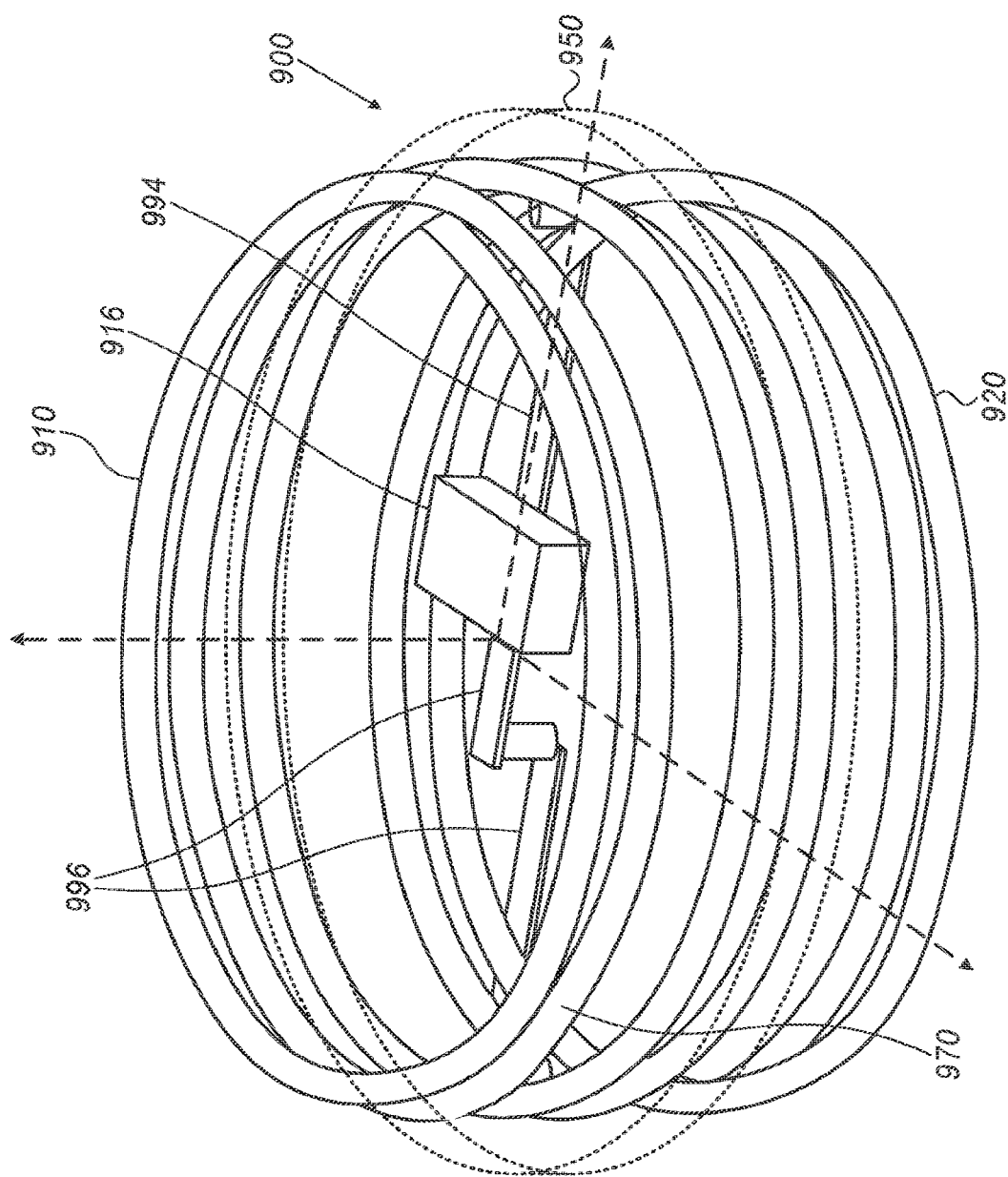
Figure 11D:
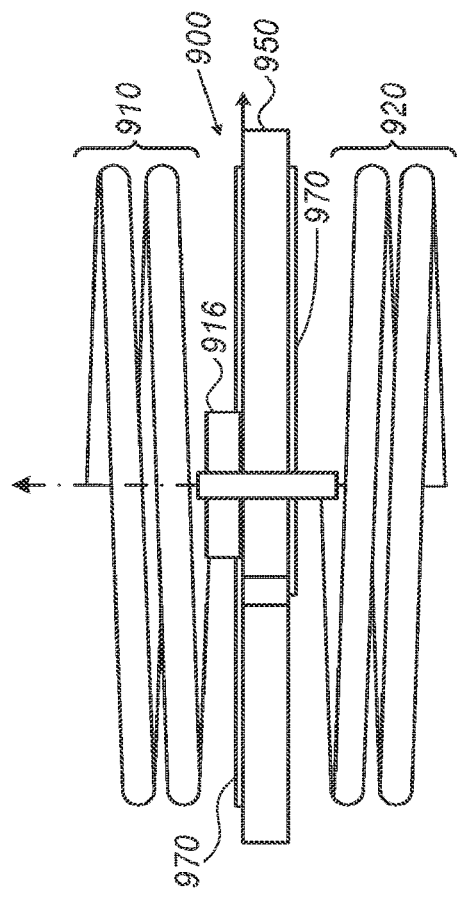
Figure 11E:
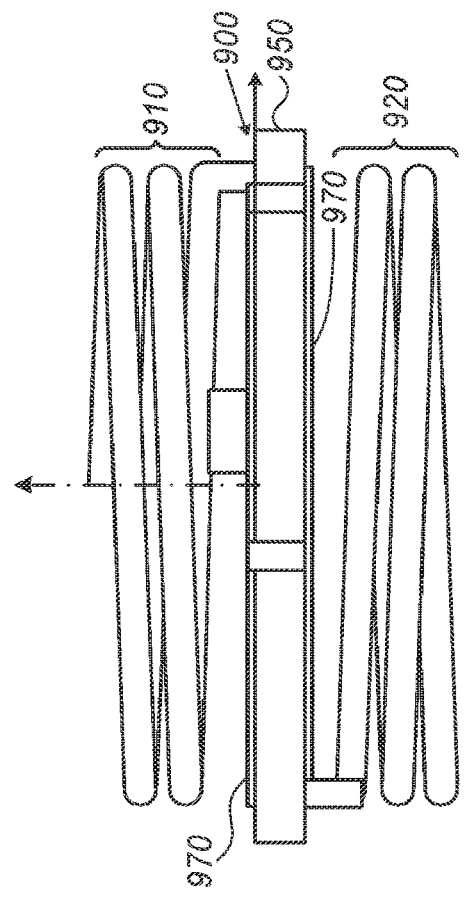
Figure 11C:
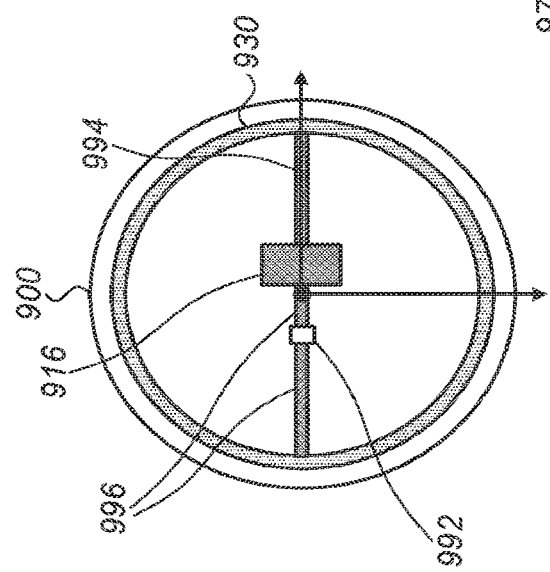

FIG. 10 shows an assembly drawing of a helix antenna 1000 according to an example embodiment. FIG. 10 is described in association with FIGS. FIG. 9A and FIGS. 9C-9D. Helix antenna 1000 includes helical conductor 910 (FIG. 9C), helical conductor 920 (FIG. 9D) and circuit board 900 (FIG. 9A). Circuit board 900 is structurally and functionally interposed between helical conductor 910 and helical conductor 920. Longitudinal axis 905 of helical conductor 910, longitudinal axis 905' of helical conductor 920 and longitudinal axis 940 of circuit board 900 may, in some embodiments, coincide (e.g., occupy the same line and orientation), substantially coincide (e.g., occupy different lines that have a same orientation), or not coincide at all (e.g., occupy lines having different orientations). For example, only two of the three longitudinal axes may coincide. For example, longitudinal axis 905 of helical conductor 910 may coincide with longitudinal axis 905' of helical conductor 920 but not with longitudinal axis 940 of circuit board 900.

To assemble helix antenna 1000, helical conductor 910 may be mounted (907) on mounting member 982, and helical conductor 920 is mounted (907') on mounting member 984. A helical conductor (e.g., helical conductor 910, 920, or both helical conductors) may be mounted on, or to, the dielectric layer of circuit board 900 (e.g., using a mounting member similar to mounting member 982 or 984) and be in electrical contact with an electrical trace of circuit board 900. Alternatively, the helical conductor(s) may be soldered to an electrical trace of circuit board 900. FIGS. 11A-11E show the assembled helix antenna 1000 from various perspectives.

An antenna feed line (e.g., feed trace or wire) that is parallel to the longitudinal axis of the helix antenna may act as a monopole antenna with its radiation destructively interfering with the helix radiation, resulting in radiation nulls areas ('dead' areas) in the radiation pattern of the antenna. Using antenna feeding line (conducting) traces that are flat and whose planes are perpendicular to the longitudinal axis of the helix antenna (e.g., antenna feeding lines, or traces, 994 and 996) to feed RF signals to the helix antenna significantly reduces the null areas. Using PCB traces as the helix antenna feeding lines (antenna feeding traces) gives flexibility in terms of the best, or optimal, size, shape and relative location of the various PCB traces and vias, and, in general, in terms of the antenna feeding lines connection to (tap) the antenna in order to optimize aspects of the performance of the helix antenna.

As described herein, due to the small size of a helix antenna (comparing to the used RF wavelength), the antenna's impedance is very low (about 1-2 ohms), making it unsuitable for use with a power amplifier ("PA"). However, as described herein, the exact location of the two antenna feeding (tap) points (e.g., points feeding 802 and 804) may be selected such that the performance of the helix antenna is optimized, for example, in terms of antenna impedance. That is, the location of the antenna's feeding points (and the electrical traces connecting the transmitter to the feeding point) may be designed such that the antenna's impedance can be increased to about 20 ohms.

Switched capacitor transmitter circuits are sometimes referred to as switched-capacitor power amplifier ("SCPA") circuits. A SCPA includes a plurality of capacitors that are switchably coupled between a power supply terminal and a reference voltage terminal (e.g., Gnd.) at a rate of the carrier frequency (e.g., 434 MHz). A wanted or desired transmission power may be predetermined for an RF power transmitter (e.g., a SCPA circuit) that is included in an in-vivo device and, using formula (1), an impedance may be calculated for a helix antenna that is to be embedded in the in-vivo device by using, or based on, the determined transmission power. Once the antenna's wanted or desired impedance is calculated, a location of a first RF feeding point and a second RF feeding point on a circuit board (e.g., circuit board 830 or circuit board 900) in the in-vivo device may be determined, and electrical traces on the circuit board may be designed so as to impart the wanted or desired calculated impedance to the helix antenna. The PA's output power, Po, is given by formula (1):

$$Po = 2*V^2/(\pi^2 * R\_antenna) \quad (1)$$

Figure 12:
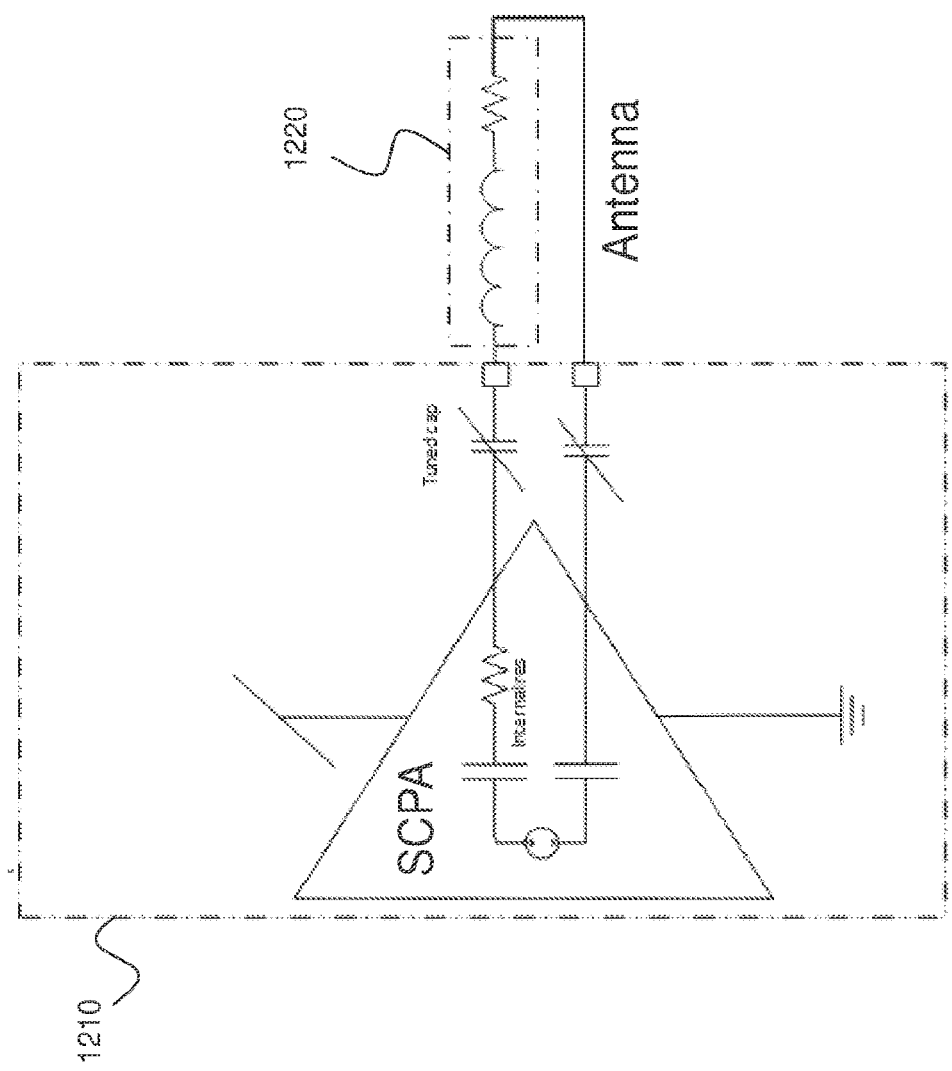
FIG. 12 schematically illustrates an example switched-capacitance power amplifier ("SCPA") for a helix antenna according to an example embodiment.

By way of example, for a 1V voltage to get a 10 mW peak power, R_antenna is equal to 20Ω, which is well above the typical small helix impedance which is approximately 1Ω (However, the helix antenna of the present invention, when properly designed, introduces an impedance that nears 20Ω) Example SCPAs are described, for example, in U.S. Patent Publication No. 2015/0381401 (titled "SWITCHED CAPACITOR TRANSMITTER CIRCUITS AND METHODS"), and in U.S. Pat. No. 6,566,933 (titled "Switched capacitor transmitter pre-driver"). A circuit board including an example SCPA power amplifier 1210 and a helix antenna 1220 (an electrically equivalent circuit) according to an example embodiment is shown in FIG. 12.

Figure 13:
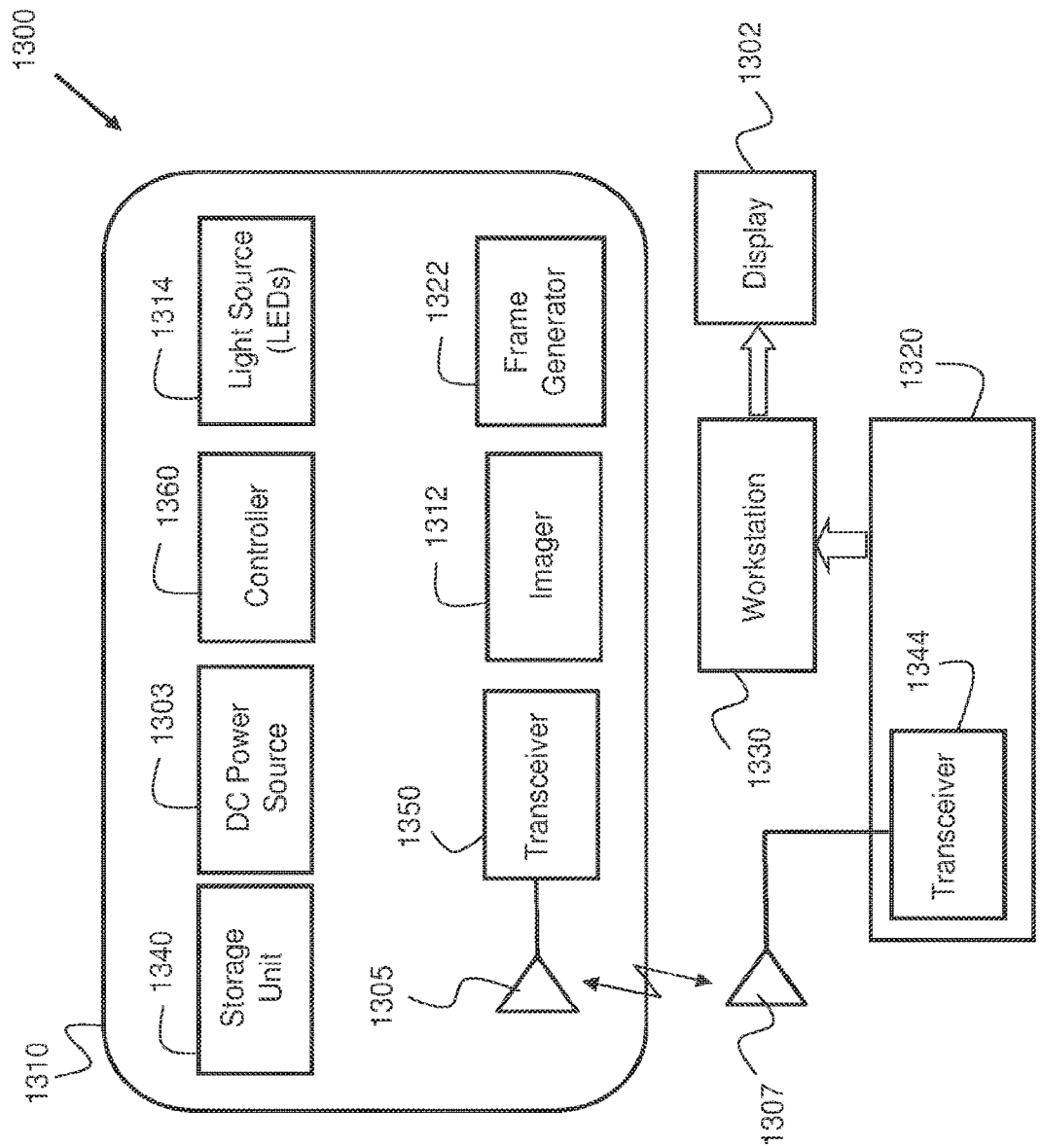
FIG. 13 schematically illustrates an example in-vivo device according to an example embodiment.

FIG. 13 shows an in-vivo system 1300 according to an example embodiment. In-vivo system 1300 includes an in-vivo device 1310 with an imager as an example sensor. Frames transmitted by or from in-vivo device 1310 may be referred to as "image frames" (although image frames may include also other types of data). In-vivo imaging system 1300 also includes a data recorder 1320 and a user workstation 1330, which may be, for example, a personal computer, and a display 1302 for displaying, for example, images and/or a video clip or moving image stream, or other data.

An in-vivo imaging device may have one or more imagers. By way of example, in-vivo imager 1310 includes one imager (e.g., imager 1312). In-vivo imager 1310 may also include a light/illumination source 1314 for illuminating a GI section to be imaged, a frame generator 1322 for producing an image frame for each captured image, a controller 1360, a storage unit 1340 for storing data (e.g., images), an RF power transmitter or transceiver 1350 for transmitting, using a helix antenna 1305, image frames (and possibly other types of data) to a receiver antenna 1307, and, optionally, for receiving data and/or commands from data recorder 1320. In-vivo imager 1310 may also include an electrical power source 1303 (e.g., a battery) for powering in-vivo device 1310.

At the time of, or shortly after, imaging device 1310 is swallowed or otherwise inserted, or after some predetermined delay (e.g., 2 minutes), imager 1312 may start capturing images of areas of the GI system. Because natural light does not enter the intestinal tract, imager 1312 does not require a light shutter, as opposed to 'regular' (i.e., non-swallowable) imagers. The function of the light shutter is, therefore, implemented by the darkness inside the intestinal tract and by intermittently illuminating the field of view ("FOV") of imager 1312. Imager 1312 may include an image sensor that may be, or include, an array of photo sensor elements (e.g., pixels) such as 256×256, 320×320, 1 Mega pixel or any other suitable array. Imager 1312 outputs image data by using a pixel format corresponding to the used pixels. Each image data may represent a captured image and, optionally, additional selected portions thereof.

Frames generator 1322 may receive image data that represents a captured image, and produce a corresponding image frame (or "frame" for short) that contains the image data. A frame typically includes a header field that contains information and/or metadata related to the frame itself (e.g., information identifying the frame, the serial number of the frame, the time the frame, the bit-wise length of the frame, etc.), and a payload field. The payload may include an uncompressed version of the image data and/or a compressed version thereof, and a decimated image.

Controller 1360 may controllably operate, among other things, illumination/light source 1314 to illuminate areas traversed by in-vivo imager 1310, and schedule the images capturing times accordingly. Controller 1360 may use a timing unit to time the operation of illumination source 1314 to illuminate, for example, four times per second to enable capturing four images per second, and the operation of transceiver 1350 to concurrently transmit corresponding frames at the same rate or at a different rate. Controller 1360 may use the timing unit to operate illumination source 1314 to capture more images per second, for example seventeen images per second, and RF power amplifier 1350 to concurrently transmit corresponding frames at the same rate or at a different rate. Controller 1360 may temporarily store captured images and related image frames in data storage unit 1340. Data recorder 1320 may be worn by the person whose GI system is to be imaged.

Data recorder 1320 may also include a receiver or transceiver 1344, a frame parser (not shown in FIG. 13), and a processor for managing them. Data recorder 1320 may include additional components (e.g., USB interface, Secure Digital ("SD") card driver/interface, controllers, etc.), elements or units for communicating with (e.g., transferring data frames, data, etc. to) a processing and/or displaying systems that may be configured to process images and localization data originating from in-vivo imager 1310, and related data. Transceiver 1344 may receive a data frame corresponding to a particular captured image, and the frame parser may parse the data frame to extract the various data contained therein (e.g., image data, decimated image associated with the particular captured image, etc.).

User workstation 1330 may include a display or be functionally connected to one or more external displays, for example to display 1302. Workstation 1330 may receive frames (e.g., image frames, localization frames, etc.) or images from data recorder 1320 and present them in real-time, for example as live video, or produce a video stream that also contains location and orientation information that may also be displayed on, for example, display 1302. Workstation 1330 may include a memory (not shown in FIG. 9) for storing the frames transferred from data recorder 1320 and possibly related metadata, and a processor (not shown in FIG. 13) for processing the stored frames and related data. Workstation 1330 may display selected images or a video clip (e.g., a moving image stream) compiled from such images, e.g., to a human operator, health care person, physician, etc. The LED driver can be adapted for any number of LEDs, including one LED.

Figure 14:
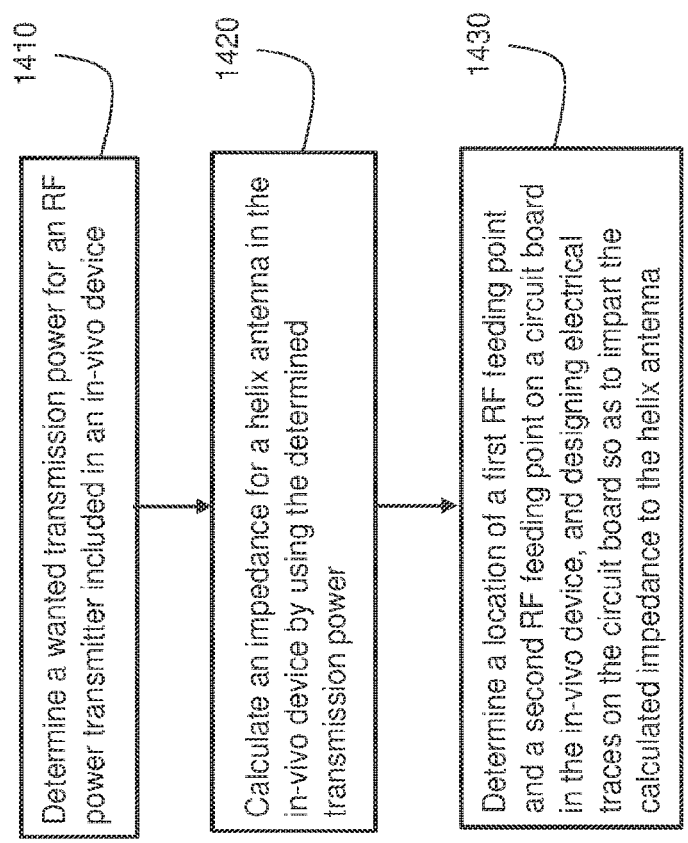
FIG. 14 shows an example method for designing a helix antenna for an in-vivo device according to an example embodiment.

FIG. 14 shows a method for designing a helix antenna for, for example, an in-vivo device according to an example embodiment. An embodiment of the method is applicable, for example, to an in-vivo device that may include an RF power transmitter (e.g., transmitters 816, 916, 1210) and a helix antenna structure (e.g., antenna structures 800, 1000), and the helix antenna structure may include a first helical conductor (e.g., conductor 810 and 910), a second helical conductor (e.g., conductor 820 and 920) and a circuit board (e.g., circuit board 830 and 900) that is structurally and functionally interposed between the first helical conductor and the second helical conductor, where the circuit board may include, among other things, a number p of circuit board layers that are (to be) orderly stacked along a longitudinal axis (e.g., axis 840, axis 940) of the circuit board. The circuit board may further include a conductor (e.g., conductor 870) having turns, where each turn includes or is an electrically conductive trace (e.g., electrical traces 860 and 960) that is disposed on, or in, a dielectric layer (e.g., 850) of a circuit board layer Li, where each conductive trace is electrically connected to a subsequent conductive trace through a via and/or blind via in the circuit board layer Li that is interposed (separates) between the conductive trace and the subsequent conductive trace. The circuit board may further include a first RF (antenna) feeding point (e.g., point 802 and 902) and a second RF feeding point (e.g., point 804 and 904) on or in the circuit board layer and respectively connectable to a first terminal and to a second terminal of the RF power transmitter via PCB electrical traces that are disposed on the PCB.

An embodiment of the method may include, per step 1410, determining a wanted or desired transmission power for an RF power transmitter (see, for example, transmitter 816 FIG. 8 and transmitter 916 FIG. 9A) that is included in an the-vivo device (e.g., in-vivo device 1310, FIG. 13), calculating, at step 1420, an antenna impedance that is suitable to obtain the determined transmission power (for example, by using formula (1)), and determining, at step 1430, a location of a first antenna feeding (tapping) point (see, for example, point 802 of FIG. 8, point 902 of FIG. 9A) and a second antenna feeding (tapping) point (see, for example, point 804 of FIG. 8, point 904 of FIG. 9A) on a circuit board (see, for example, circuit board 830 of FIG. 8 and circuit board 900 of FIG. 9A) intended to accommodate the RF power transmitter in the in-vivo device so as to impart the calculated impedance to a helix antenna that is to be embedded in the in-vivo device. Optionally, or if required, electrical traces may be designed on the circuit board in order to obtain the calculated impedance. (That is, according to some embodiments, there may be a tradeoff between the location of a first and second antenna feeding points and the electrical trace design disposed on and/or in the circuit board.)

An embodiment of the method is also applicable to a helix antenna that includes an electrical conductor as in FIG. 15, and that is completely mounted on, incorporated into or embedded in a multilayered PCB as exemplified in FIGS. 16, 17A-17B, 18A-18B and 19A-19B, which are described below.

FIG. 15 shows example helix loop antennas (antenna turns) 1500 for a FPHA according to an example embodiment. In this embodiment all of loop antennas 1500 collectively realize the loop antennas of the NMHA model shown in FIG. 6, and all of them are incorporated into a multilayered PCB. In other embodiments, only some (e.g., a midsection) of the helix turns (loop antennas) realize the NMHA model and incorporated into a multilayered PCB, while the other helix turns (loop antennas) are 'regular' coiled (spiraling, helical) turns of a helical conductor.

Each antenna turn (loop antenna) of antenna turns 1500 may be flat (e.g., because it is implemented as a flat PCB trace) and function-wise resembles a loop antenna. Loop antennas 1500 may be connected to one another by using conducting 'bridges'. An antenna 'bridge' may be implemented, for example, as a PCB via, or as a PCB (electrically conducting) trace, and the like, and it resembles (functions as) a monopole antenna. (The spatial arrangement of loop antennas 1500, including the antenna turns and connecting bridges that connect the antenna turns, resembles, or implements, the model of the NMHA. (The NMHA model is a superposition of monopoles and loop antennas, as described in connection with, and shown in, FIG. 6.)

PCB layers, which, when operational, are longitudinally stacked, accommodate loop antennas 1500 and the bridges. (The PCB layers are not shown in FIG. 15 in order not to obscure the antenna's turns and connecting bridges.) By way of example, loop antennas 1500 include six PCB traces as antenna turns (as loop antennae) which are orderly designated as n1, n2, n3, n4, n5 and n6, with the conductive trace n1 shown at the top and forming the top antenna turn. "n1–s" is a 'starting' point of antenna turn n1, "n2–s" is a starting point of antenna turn n2, "n3–s" is a starting point of antenna turn n3, "n4–s" is a starting point of antenna turn n4. (The starting points of antenna turns n5 and n6 are not indicated.) The number of PCB traces (loop antennas) of a FPHA may be less than six, though this may result in degradation in the performance of the antenna, or greater than six, if allowable by space constraints.

Beneath conductive trace n1 is shown the next conductive trace n2, which forms another antenna turn. Beneath conductive trace n2 is shown the next conductive trace n3, which forms another antenna turn. Beneath conductive trace n3 is shown the next conductive trace n4, which forms another antenna turn. Beneath conductive trace n4 is shown the next conductive trace n5, which forms another antenna turn, and beneath conductive trace n5 is shown the next conductive trace n6, which forms another antenna turn. (The number of antenna turns may vary according to physical and/or electrical (e.g., functional) constraints and/or according to the application or requirement.) Loop antennas 1500 is referred to herein as a "full PCB helix antenna structure" (FPHA) because every conductive element of the antenna (e.g., loop antennas, bridges that connect loop antenna) is printed on or embedded in one of the PCB's layers, or is connecting two PCB layers. Antenna 'tail' 1560 makes an exception in this regard.

PCB conductive traces n1 through n6 may be parallel (or substantially parallel), and they are, in this example, interconnected by using five bridges which are designated as b1, b2, b3, b4 and b5. (A 'bridge' may be implemented as a PCB via or as a flexible PCB conductive trace.) Each PCB conductive trace, ni, may be connected to a lower conductive trace, ni+1, and/or to an upper conductive trace, ni−1, by a PCB via (for example bridge b3 is a "via" connection), or via a flexible PCB trace (for example bridges b1, b2, b4 and b5 are flexible connections).

Two 'adjacent' loop antennas (which are PCB conductive traces) may be printed on a same PCB layer (one loop antenna on each side of the PCB layer), or on separate PCB layers. Some of the PCB layers may include loop antennas on both sides while other PCB layers may include a loop antenna only on one side. All or some of the PCB layers may include loop antennas on both sides, and some PCB layers may include a loop antenna only on one side of the PCB layers. Some, or all, of the antenna turns (e.g., antenna turns n1-n6) may be fully or partly embedded in PCB layers. Some, or all, of the PCB layers may be flexible. Some, or all, of the PCB layers may be rigid. Regardless of the rigidness of the PCB layers, the PCB layers may be connected to one another using flexible sections.

Inside loop antennas 1500 are two radial (or 'semi-radial') antenna feeding lines 1510 and 1520 (including a 'bridging' trace line 1522 which may be regarded as part, or as an 'extension', of trace line 1520) that connect two of the loop antennas 1500 to output terminals of transmitter 1530. (Transmitter 1530 is accommodated by (e.g. mounted in or on) a selected PCB layer, though the selected PCB layer itself is not shown in FIG. 15.) Antenna feeding line 1510 (a first antenna feeding line) may be electrically connected to the loop antenna (e.g., loop antenna n3) mounted in or on a selected printed circuit board layer and electrically connectable to a first output terminal of a transmitter (e.g., transmitter 1530). Antenna feeding line 1520 (a second antenna feeding line) may be electrically connected to a second loop antenna (e.g., loop antenna n4) that is not mounted in or on the selected printed circuit board layer, but is electrically connectable, e.g., via 'intermediate' feeding line 1522, to a second output terminal of the transmitter.

Antenna feeding lines 1510 and 1520 may be PCB traces. Antenna feeding line 1510 may inwardly (e.g., radially, semi-radially or curvedly) split off (and connected to) one loop antenna (in this example it is split off loop antenna n3), and the distal (innermost) end of PCB conductive trace 1510 may be connected to an output terminal of transmitter 1530. Transmitter 1530 resides inside the loop antenna that is mounted or printed on the PCB layer accommodating the transmitter. For example, transmitter 1530 may be centered in the loop antenna (e.g., it may coincide with longitudinal axis 1502 of loop antennas 1500), or it may be offset from the longitudinal axis by some extent.

Antenna feeding line 1520 (of which PCB trace 1522 is part) is a PCB trace that is inwardly (e.g., radially, semi-radially or curvedly) split off a different loop antenna (in this example it is split off loop antenna n4). The distal (innermost) end of PCB conductive trace 1520 is connected to a second output terminal of transmitter 1530, though it is connected to this output terminal via a 'bridging' trace 1522. (Bridging trace 1522 and PCB trace 1520 are connected through a PCB via at 1540.)

In accordance with the invention, antenna feeding lines 1510 and 1520 (including bridging trace line 1522) preferably radially lie in an X-Y plane that is perpendicular to the Z-coordinate. (The Z-coordinate corresponds to, or represents, the longitudinal axis (1502) of loop antennas 1500.) In addition, the number of antenna turns may be less or greater than six, and the transmitter (e.g., transmitter 1530) may be located anywhere in the inner space of loop antennas 1500 (the space circumscribed by, or confined by, loop antennas 1500), provided that the antenna's feeding lines, when connected to the transmitter and during operation of the transmitter, lie in the X-Y plane, in order to make them perpendicular to the longitudinal axis 1502 (e.g., corresponding to the Z-axis) of loop antennas 1500. (Whenever the term "antenna turn" is mentioned herein in connection with a structure of a PCB, it also means a "loop antenna" within the context of the model of the NMHA, per FIG. 6.)

An axial, 'tail' like, antenna extension 1560 may lengthwise (axially) extend away from loop antennas 1500 and from transmitter 1530 and be, for example, parallel to longitudinal axis 1502 of loop antennas 1500. Antenna extension 1560 may be connected to distal end 1550 of the last antenna turn (e.g., antenna turn n6). Alternatively, an antenna extension similar to antenna extension 1560 may be connected to a start point of the first antenna turn, for example to start point n1–s (the turn's distal end) of first antenna turn n1.

FIG. 16 shows helix loop antennas 1500 of FIG. 15 integrated into a multilayered PCB to form a FPHA according to an example embodiment. Reference numerals used in FIG. 15 are used in FIG. 16 for ease of reference. (Like reference numerals denote similar elements between FIGS. 15 and 16.) (The multilayered PCB is not shown clearly in FIG. 16, but a spread out version of a similar multilayered PCB is clearly shown, for example, in FIGS. 17A and 17B.

The FPHA may be incorporated in an in-vivo device. The in-vivo device incorporating the FPHA may also include an imager (imaging sensor) 1610 and, for full PCB helix antenna structure 1500 may also include additional components, for example a light source (e.g., light emitting diodes (LEDs)), various electronic chips (e.g., processor, data storage unit, analog-to-digital converter ("ADC"), digital-to-analog converter ("DAC"), transceiver, etc.), however these circuit elements are not shown in FIG. 16 in order not to further obscure the FPHA.

Figure 17A:
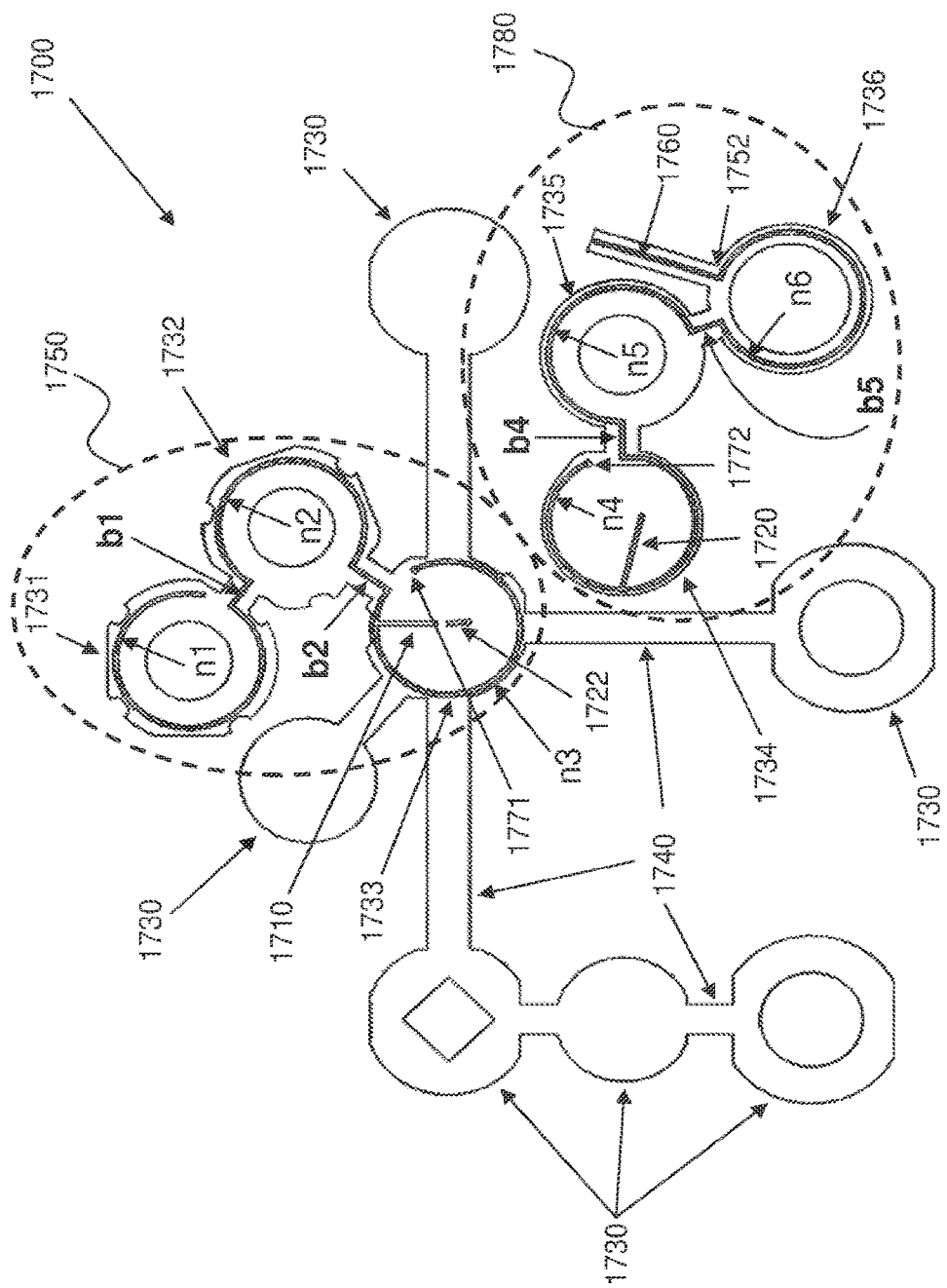
FIGS. 17A and 17B depict an example spread out PCB for a FPHA according to an example embodiment.
Figure 17B:
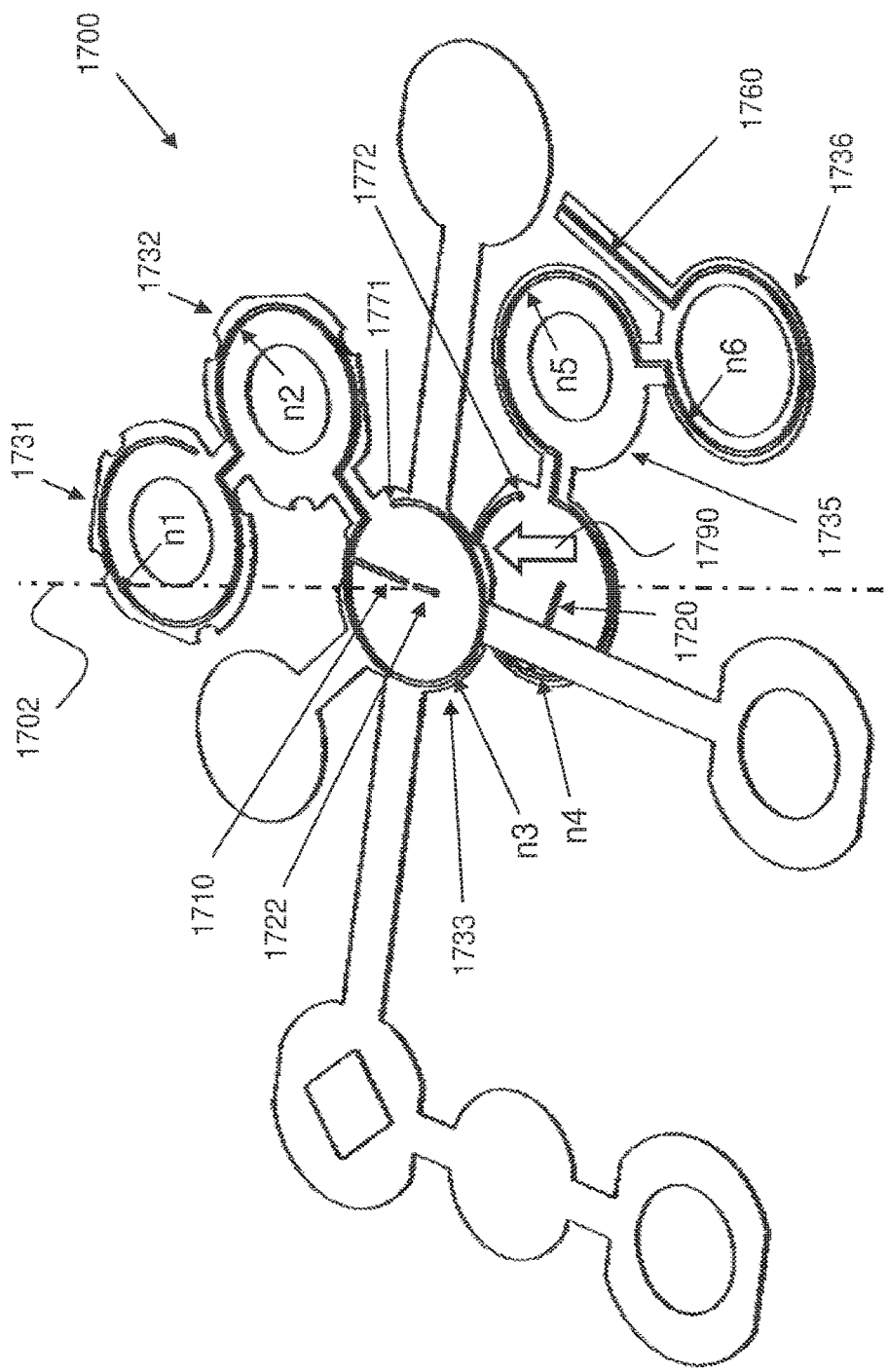

FIGS. 17A-17B depict a spread out of multilayered PCB 1700 for a FPHA according to an example embodiment. Reference numerals used in FIG. 17A are used in FIG. 17B as well for ease of reference. (Like reference numerals denote similar elements between FIGS. 17A and 17B.) (PCBs having different layouts than the layout of PCB 1700 may be used.)

Multilayered PCB 1700 includes several PCB installation units, which are shown, for example, at 1730. Installation units may be interconnected by using PCB connection sections such as the ones shown at 1740. PCB 1700 may include a first 'integral' antenna PCB section 1750 that includes three PCB layers, or installation units, which are designated as 1731, 1732 and 1733, on which, or in which, antenna turns n1, n2 and n3 may respectively be mounted or printed. (Antenna PCB section 1750 is an integral part of PCB 1700 because one of its PCB layers, or installation units, in this example PCB layer (installation unit) 1733, is connected to at least one installation unit of PCB section 1700 by a PCB connection section (e.g., 1740).)

PCB 1700 also includes a separate, or annexed, antenna PCB section 1780 that also includes three PCB layers, or installation units, which are designated as 1734, 1735 and 1736, on which, or in which, antenna turns n4, n5 and n6 may respectively be mounted or printed. (Antenna PCB section 1780 is a separate PCB part, or an 'annexed' PCB part, of PCB 1700 because antenna PCB section 1780 is, or can be, manufactured as a separate PCB part, though it is electrically connected to the 'main' PCB (e.g., to other part(s) of the greater PCB) during the PCB assembling process, during which antenna PCB sections 1750 and 1780 may be fixed in place (by using, for example, plastic spacers), and electrically (functionally) connected via a PCB 'bridge' (e.g., PCB via, flexible PCB trace).) Antenna turns n1 through n6 are peripheral loop antennas that may be respectively mounted on six PCB layers. (A "peripheral loop antenna" is a loop antenna that is mounted on the periphery of a PCB layer, or adjacent to the periphery of the PCB layer.)

Also shown in FIG. 17A are connection bridge b1, which connects antenna turns n1 and n2, connection bridge b2, which connects antenna turns n2 and n3, connection bridge b4, which connects antenna turns n4 and n5, and connection bridge b5, which connects antenna turns n5 and n6. When antenna PCB sections 1750 and 1780 are assembled (e.g., during or part of their assembling process), the two antenna PCB sections are connected by another connection bridge (connection bridge b3, which is not shown in FIG. 17A but a similar connection bridge is shown, for example, in FIG. 15).

PCB layer (an installation unit) 1733 may include an antenna feeding line 1710 similar to antenna feeding line 1510 in FIG. 15, and a bridging trace line 1722 similar to bridging trace line 1522 in FIG. 15. During, or as part of, the assembling process of PCB 1700, a transmitter (not shown in FIG. 17A but shown, for example, in FIG. 15; e.g., transmitter 1530) is mounted on a selected PCB layer (an installation unit) 1733, and electrically (functionally) connected to antenna feeding line 1710 and to bridging trace line 1722. Installation unit 1734 may include an antenna feeding line 1720 similar to antenna feeding line 1520 in FIG. 15. (Bridging trace line 1722 is an extension line (it is part) of antenna feeding line 1720.) While a first antenna feeding line (e.g., antenna feeding line 1710) may be mounted in or on a selected PCB layer (e.g., PCB layer 1733), a second antenna feeding line may be partly mounted in or on a non-selected PCB layer (e.g., as feeding line 1720 on PCB layer 1734) and partly mounted in or on the selected PCB layer (e.g., as a bridging feeding line 1722 on PCB layer 1733.) Since PCB layer 1733 is designed to accommodate a transmitter (e.g. the PCB layer may include a space for the transmitter and antenna feeding lines 1710 and 1722 to which the transmitter is to be connected), PCB layer 1733 is regarded as a "selected PCB layer".

A transmitter mounted on PCB layer or installation unit 1733 and electrically connected to antenna feeding line 1710 and to bridging trace line (an antenna feeding line) 1722 (which is part of antenna feeding line 1720, though on a different PCB layer) can transfer RF power to the helix antenna via these feeding lines. (The PCB layer, or installation unit, that physically and electrically accommodate the transmitter; e.g., powers the transmitter and enables it to transfer data and/or signals, is referred to herein as "selected PCB layer".) A selected PCB layer is configured to physically and electrically accommodate a transmitter inside the peripheral loop antenna related to the selected PCB layer. For example, PCB layer 1733 includes peripheral loop antenna n3, and PCB layer 1733 is configured to physically and electrically accommodate a transmitter inside peripheral loop antenna n3. (The transmitter itself is not shown in FIGS. 17A-17B. It is shown, however, for example, in FIGS. 18A-18B at 1852.)

Antenna feeding line 1710 (a first antenna feeding line) may be electrically connected to the loop antenna (e.g., loop antenna n3) disposed in or on a selected printed circuit board layer 1733 and electrically connectable to a first output terminal of a transmitter (not shown in FIG. 17A). Antenna feeding line 1720 (a second antenna feeding line) may be electrically connected to a second loop antenna (e.g., loop antenna n4) that is not disposed in or on the selected printed circuit board layer (1733), but, rather, in or on, for example, printed circuit board layer 1732, and feeding line 1720 is electrically connectable, via 'intermediate' feeding line 1722, to a second output terminal of the transmitter.

Each of antenna feeding line 1710 and 1720 extends radially, or semi-radially, from the antenna turn on or in the respective PCB layer (PCB installation unit). ("Semi-radially"-'somewhat' radially, for example an antenna feeding line extending from a point near the center point of the related PCB layer or peripheral loop antenna to a point on the peripheral loop antenna.) The two antenna feeding lines may be mounted on, formed in or be embedded in separate PCB layers, and they may, for example, be may be mounted on, formed in or be embedded in adjacent PCB layers (e.g., with no other PCB layer interposed between them), or they may be mounted on, formed in or be embedded in PCB layers which are spaced apart (e.g., with one or more PCB layers interposed between them).

Regardless of their location in the PCB structure, the two antenna feeding lines lie in or on PCB layer 1733, or in or on PCB layer 1733 and another, parallel, PCB layer which is(are) perpendicular to longitudinal axis 1702 (see FIG. 17B) of PCB 1700. PCB 1700 may be foldable such that, after folding it (in the folded state), the plurality of PCB layers are lengthwise stacked along longitudinal axis 1702 and ordered from a first PCB layer (e.g., PCB layer 1731) that includes a first loop antenna n1 to a last PCB layer (e.g., PCB layer 1736) that includes a last loop antenna (e.g., antenna feeding lines n6).

The helix antenna may further include a first helical conductor (which may be similar to, for example, helical conductor 810) that may be electrically connected to the first loop antenna. The helix antenna may further include a second helical conductor (which may be similar to, for example, helical conductor 820) that may be electrically connected to the last loop antenna.

PCB 1700 may also be foldable such that the first antenna feeding line (e.g., antenna feeding line 1710) and the second antenna feeding line (e.g., antenna feeding lines 1720) respectively lie in the selected PCB layer (e.g., PCB layer 1733), or their respective PCB layers (e.g., in the selected PCB layer and in a non-selected PCB layer), which, after assembling of PCB 1700, are all perpendicular to longitudinal axis 1702. (PCB 1700 of FIGS. 17A-17B is shown in folded state in FIGS. 18A-18B, and 19A-19B.) The selected PCB layer may be lengthwise located in a middle section of the multilayered PCB.

The helix antenna mounted or printed in PCB sections 1750 and 1780 may include a 'tail' like antenna extension 1760. Antenna extension 1760 may be electrically connected to a distal end 1752 of the last antenna turn (e.g., antenna turn n6). After folding PCB 1700, antenna extension 1760 may axially extend away from the transmitter, in parallel to longitudinal axis 1702 and, which, during operation of PCB 1700, resides in, or is accommodated by, selected PCB layer 1733. Longitudinal axis 1702 is a longitudinal axis of the folded antenna structure (PCB sections 1750 and 1780), and, after PCB 1700 is completely folded, of entire PCB 1700.

FIG. 17B shows PCB 1700 with separate antenna PCB section 1780 (see FIG. 17A) lying underneath integral antenna PCB section 1750 (see FIG. 17A). Assembling of the PCB may include attaching (1790) antenna PCB section 1780 to antenna PCB section 1750, by means of, for example, a plastic spacer, such that a distal end 1771 of antenna turn n3 is spatially positioned above a distal end 1772 of antenna turn n4, so that the two distal ends (1771, 1772) can be electrically connected through a PCB via or by means of a flexible trace (which are referred to herein as bridge b3), and antenna feeding lines 1720 and 1722 can be electrically connected through a PCB via. During assembling of the PCB structure, the various PCB layers (installation units) are folded such that they form two, lengthwise stacked, imaging 'heads' that can take pictures in opposite directions.

FIGS. 18A-18B depict an example spread out PCB 1800 for a FPHA according to an example embodiment. FIG. 18A depicts a spread out PCB structure 1800 in a first assembly state, and FIG. 18B depicts the spread out PCB structure 1800 of FIG. 18A in a more advanced assembly state, as described below.

Referring to FIG. 18A, spread out PCB 1800 may include a first optical head 1810 and a second optical head 1820. Optical head 1810 is shown spread out, and optical head 1820 is shown in a more advanced assembly state. Optical head 1810 may include three PCB layers (installation units), for example one PCB layer to accommodate an image sensor and lenses that are lengthwise stacked in a housing, as shown at 1830; another PCB layer to accommodate a light source (for the image sensor), as shown at 1840, and another PCB layer to accommodate a first battery contact coil, as shown at 1870. (The image sensor and lenses are not shown in FIGS. 18A-18B.) Optical head 1810 resembles optical head 1820 after its PCB layers are folded. The light source related to optical head 1820 is accommodated by a separate PCB layer, as shown at 1842. Each light source may include multiple LEDs, some of which are shown at 1844. Separate antenna PCB section 1880 is shown in a 'spread out' state in FIG. 18A and assembled in FIG. 18B, with the tail like antenna extension 1860 axially lengthwise extends away from transmitter 1852, in parallel to longitudinal axis 1802 of the antenna structure.

FIGS. 19A and 19B depict an optical head 1900 of an in-vivo device that includes a FPHA similar to the FPHA of FIGS. 17A-17B (FPHA 1700) and FIGS. 18A-18B (FPHA 1800). (An in-vivo device may include a FPHA with a different layout.) The reference numerals, PCB layers designation (n1, n2, and so on), and bridges (b1, b2, and so on) that are used in FIG. 19A correspond to the same elements in FIGS. 17A-17B and FIGS. 18A-18B. FIG. 19B shows the imaging head 1900 of FIG. 19A from a different perspective.

A device, system and methods in accordance with some embodiments of the invention may be used, for example, in conjunction with a device which may be implanted or swallowed.

However, the scope of the present invention is not limited in this regard. For example, the helix antenna structure disclosed herein may be used to receive sensory information from small tools and small (e.g., miniature) toys as well as to transmit control signals to such devices.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A helix antenna structure comprising: multilayered printed circuit board comprising; a plurality of printed circuit board layers, each printed circuit board layer comprising a peripheral loop antenna, a plurality of connection bridges, each connection bridge connecting two peripheral loop antennas, wherein the multilayered printed circuit board is foldable; and wherein a selected one of the printed circuit board layers is configured to physically and electrically accommodate a transmitter inside the peripheral loop antenna of the selected printed circuit board layer, the selected printed circuit board layer comprising a first antenna feeding line, the first antenna feeding line splitting off from the peripheral loop antenna of the selected printed circuit board layer and configured to be electrically connected to a first output terminal of the transmitter; and an antenna extension, said antenna extension electrically connected to a last peripheral loop antenna and axially extending away from the plurality of printed circuit board layers.

2. The helix antenna structure as in claim 1, wherein the multilayered printed circuit board further comprises a second antenna feeding line splitting off from a second peripheral loop antenna and configured to be electrically connected to a second output terminal of the transmitter.

3. The helix antenna structure as in claim 2, wherein the second antenna feeding line is partly disposed on the selected printed circuit board layer and partly disposed on a non-selected printed circuit board layer.

4. The helix antenna structure as in claim 2, wherein the entire second antenna feeding line is disposed on a non-selected printed circuit board layer.

5. The helix antenna structure as in claim 2, wherein, in the folded state, the plurality of printed circuit board layers are lengthwise stacked along a longitudinal axis and ordered from a first printed circuit board layer comprising a first peripheral loop antenna to a last printed circuit board layer comprising the last peripheral loop antenna, and such that the first antenna feeding line and the second antenna feeding line lie in a plane perpendicular to the longitudinal axis.

6. The helix antenna structure as in claim 5, wherein the selected printed circuit board layer is lengthwise located in a middle section of the multilayered printed circuit board.

7. The helix antenna structure as in claim 5, wherein each circuit board layer has a thickness W equal to S, or within the range S±5%, wherein S is spacing between turns of the peripheral loop antennas.

8. The helix antenna structure as in claim 2, wherein the selected printed circuit board layer further comprises the transmitter.

9. The helix antenna structure as in claim 1, wherein the plurality of connection bridges is selected from the group consisting of: a printed circuit board via, a printed circuit board blind via, and a printed circuit board conductive trace.

10. The helix antenna structure as in claim 1, wherein the printed circuit board layers are circular with a diameter D1, where D1≤15 millimeters.

11. A printed circuit board for a helix antenna structure comprising: a plurality of printed circuit board layers, each printed circuit board layer comprising a peripheral loop antenna and a plurality of connection bridges, each connection bridge connecting two peripheral loop antennas, wherein the printed circuit board is foldable, and wherein a selected one of the printed circuit board layers being configured to physically and electrically accommodate a transmitter inside the peripheral loop antenna related to the selected printed circuit board layer; a first antenna feeding line disposed on the selected printed circuit board layer and splitting off from the peripheral loop antenna of the selected printed circuit board layer and configured to be electrically connected to a first output terminal of the transmitter; a second antenna feeding line splitting off from another peripheral loop antenna and electrically connectable to a second output terminal of the transmitter; and an antenna extension, said antenna extension electrically connected to a last peripheral loop antenna and axially extending away from the plurality of printed circuit board layers.

12. The printed circuit board as in claim 11, wherein the second antenna feeding line is partly disposed on the selected printed circuit board layer and partly disposed on a non-selected printed circuit board layer.

13. The printed circuit board as in claim 11, wherein the second antenna feeding line is entirely disposed on a non-selected printed circuit board layer.

14. The printed circuit board as in claim 11, wherein, in the folded state, the plurality of printed circuit board layers are lengthwise stacked along a longitudinal axis and ordered from a first printed circuit board layer comprising a first peripheral loop antenna to a last printed circuit board layer comprising a last peripheral loop antenna, and such that the first antenna feeding line and the second antenna feeding line lie in a plane perpendicular to the longitudinal axis, and wherein the selected printed circuit board layer is lengthwise located in a middle section of the printed circuit board.

* * * * *